US011566213B2

(12) United States Patent
Allbritton et al.

(10) Patent No.: US 11,566,213 B2
(45) Date of Patent: *Jan. 31, 2023

(54) DISSOLUTION GUIDED WETTING OF STRUCTURED SURFACES

(71) Applicant: The University of North Carolina at Chapel Hill, Chapel Hill, NC (US)

(72) Inventors: Nancy L. Allbritton, Chapel Hill, NC (US); Yuli Wang, Cary, NC (US); Christopher Sims, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 370 days.

This patent is subject to a terminal disclaimer.

(21) Appl. No.: 16/525,191

(22) Filed: Jul. 29, 2019

(65) Prior Publication Data

US 2020/0231917 A1 Jul. 23, 2020

Related U.S. Application Data

(63) Continuation of application No. 15/995,360, filed on Jun. 1, 2018, now Pat. No. 10,364,411, which is a (Continued)

(51) Int. Cl.
*C12M 3/06* (2006.01)
*B01L 3/00* (2006.01)
(Continued)

(52) U.S. Cl.
CPC ........... *C12M 23/16* (2013.01); *B01L 3/5027* (2013.01); *B01L 3/502707* (2013.01);
(Continued)

(58) Field of Classification Search
CPC ...... C12M 23/16; C12M 23/12; C12M 29/20; B81C 1/00206; B01L 3/502707;
(Continued)

(56) References Cited

U.S. PATENT DOCUMENTS 5,368,634 A 11/1994 Hackett
5,512,131 A 4/1996 Kumar et al.
(Continued)

FOREIGN PATENT DOCUMENTS

EP 2436446 4/2012
GB 2462364 2/2010
(Continued)

OTHER PUBLICATIONS

Abdelsalam, M.E., et al., Wetting of Regularly Structured Gold Surfaces, Langmuir, 2005, pp. 1753-1757, vol. 21.
(Continued)

*Primary Examiner* — Dennis White
(74) *Attorney, Agent, or Firm* — Jenkins, Wilson, Taylor & Hunt, P.A.

(57) ABSTRACT

A microfabricated device having at least one gas-entrapping feature formed therein in a configuration that entraps air bubbles upon wetting the feature with a solvent or solution is described. The device includes a sacrificial residue in contact with the gas-entrapping feature, the dissolution of which guides the wetting of the gas-entrapping feature.

23 Claims, 11 Drawing Sheets

Related U.S. Application Data continuation of application No. 14/404,225, filed as application No. PCT/US2013/043562 on May 31, 2013, now Pat. No. 9,994,805.

(60) Provisional application No. 61/653,783, filed on May 31, 2012.

(51) Int. Cl.
*G01N 35/00* (2006.01)
*B81C 1/00* (2006.01)
*C12Q 1/02* (2006.01)
*C12M 1/00* (2006.01)
*C12M 1/32* (2006.01)

(52) U.S. Cl.
CPC ......... *B81C 1/00206* (2013.01); *C12M 23/12* (2013.01); *C12M 29/20* (2013.01); *C12Q 1/02* (2013.01); *B01L 2200/0684* (2013.01); *B01L 2200/12* (2013.01); *B01L 2300/161* (2013.01); *B81B 2201/058* (2013.01); *G01N 2035/00158* (2013.01)

(58) Field of Classification Search
CPC ............... B01L 3/5027; B01L 2200/12; B01L 2200/0684; B01L 2300/161; B81B 2201/058; G01N 2035/00158; C12Q 1/02
See application file for complete search history.

(56) References Cited

U.S. PATENT DOCUMENTS

| | | | |
|---|---|---|---|
| 5,885,470 | A | 3/1999 | Parce et al. |
| 6,103,446 | A | 8/2000 | Devlin et al. |
| 6,596,346 | B2 | 7/2003 | Bernard et al. |
| 6,627,159 | B1 | 9/2003 | Bedingham et al. |
| 6,632,655 | B1 | 10/2003 | Mehta et al. |
| 6,645,432 | B1 | 11/2003 | Anderson |
| 6,670,133 | B2 | 12/2003 | Knapp et al. |
| 6,919,058 | B2 | 7/2005 | Andersson et al. |
| 6,966,997 | B1 | 11/2005 | Inganas |
| 7,161,356 | B1 | 1/2007 | Chien |
| 7,169,577 | B2 | 1/2007 | Wang et al. |
| 7,556,776 | B2 | 7/2009 | Fraden et al. |
| 7,572,841 | B2 | 8/2009 | Chen et al. |
| 7,742,662 | B2 | 6/2010 | Cunningham |
| 7,775,088 | B2 | 8/2010 | Ruby |
| 7,927,830 | B2 | 4/2011 | Cheung et al. |
| 8,318,439 | B2 | 11/2012 | Battrell et al. |
| 8,357,616 | B2 | 1/2013 | Linder |
| 8,772,017 | B2 | 7/2014 | Battrell et al. |
| 10,364,411 | B2 | 7/2019 | Allbritton et al. |
| 2004/0171135 | A1 | 9/2004 | Ostuni |
| 2005/0054078 | A1* | 3/2005 | Miller ............... B01L 3/502707 435/287.1 |
| 2006/0228263 | A1 | 10/2006 | Berndtsson |
| 2007/0062594 | A1 | 3/2007 | Extrand |
| 2007/0280857 | A1 | 12/2007 | Song et al. |
| 2009/0126568 | A1 | 5/2009 | Karaki et al. |
| 2010/0093105 | A1 | 4/2010 | Lee |
| 2011/0123413 | A1 | 5/2011 | Abate et al. |

FOREIGN PATENT DOCUMENTS

| | | |
|---|---|---|
| JP | H05306683 | 11/1993 |
| JP | 2005334872 | 12/2005 |
| JP | 2006518837 | 8/2006 |
| JP | 2006242607 | 9/2006 |
| JP | 2007043998 | 2/2007 |
| JP | 2008082961 | 4/2008 |
| JP | 2011160728 | 8/2011 |
| JP | 2013090586 | 5/2013 |
| WO | WO0149414 | 7/2001 |
| WO | WO2006132640 | 12/2006 |
| WO | WO2007002480 | 1/2007 |
| WO | WO 2010053951 | 5/2010 |
| WO | WO2011103143 | 8/2011 |
| WO | WO2012010653 | 1/2012 |
| WO | WO2013/181506 | 12/2013 |

OTHER PUBLICATIONS

Bodas D. and Khan-Malek, C. Microelectronic Engineering, 2006, 83, 1277-1279.
Bodas, D., et al., Hydrophilization and hydrophobic recovery of PDMS by oxygen plasma and chemical treatment—An SEM investigation, Sensors and Actuators B, 2007, pp. 368-373, vol. 123.
Bormashenko, E., et al., Vibration-induced Cassie-Wenzel wetting transition on rough surfaces, Applied Physics Letters, 2007, pp. 201917-1-201917-2, vol. 90.
Bormashenko, E., Wetting transitions on biometric surfaces, Philosophical Transactions of the Royal Society A, 2010, pp. 4695-4711, vol. 368.
Charnley, M., et al., Integration column: microwell arrays for mammalian cell culture, Integrative Biology, 2009, pp. 625-634, vol. 1.
Fritz, J.L., et al., Hydrophobic Recovery of Plasma-Treated Polydimethylsiloxane, The Journal of Adhesion, 1995, pp. 33-45, vol. 54.
Gach, P.C., et al., Isolation and manipulation of living adherent cells by micromolded magnetic rafts, Biomicrofluidics, 2011, pp. 032002-1-032002-12, vol. 5.
Horvath, R., et al., Fabrication of all-polymer freestanding waveguides, Journal of Micromechanics and Microengineering, 2003, pp. 419-424, vol. 13.
Hsieh, C.H., et al., Patterned PDMS based cell array system: a novel method for fast cell array fabrication, Biomed Microdevices, 2010, pp. 897-905, vol. 12.
Hu, S., et al., Surface Modification of Poly(dimethylsiloxane) Microfluidic Devices by Ultraviolet Polymer Grafting, Analytical Chemistry, 2002, pp. 4117-4123, vol. 74.
Intent to Grant corresponding to European Patent Application No. 13796502.6 dated Feb. 11, 2020.
Ishino, C., et al., Wetting transitions on rough surfaces, Europhysics Letters, 2004, pp. 419-425, vol. 68, No. 3.
Isotupa, K.P., et al., Effect of polyol gums on dental plaque in orthodontic patients, American Journal of Orthodontics and Dentofacial Orthopedics, May 1995, pp. 497-504, vol. 107, No. 5.
Jokinen, V., et al., Oxygen and nitrogen plasma hydrophilization and hydrophobic recovery of polymers, Biomicrofluidics, 2012, pp. 016501-1-016501-10, vol. 6.
Kang, J.H., et al., Analysis of pressure-driven air bubble elimination in a microfluidic device, Lab on a Chip, 2008, pp. 176-178, vol. 8.
Kovarik, M.L., et al., Micro Total Analysis Systems for Cell Biology and Biochemical Assays, Analytical Chemistry, 2011, pp. 516-540, vol. 84.
Micro Chem, Nano SU-8, 2002, 4 pages.
Moeller, H.C., et al., A microwell array system for stem cell culture, Biomaterials, Feb. 2008, pp. 752-763, vol. 29, No. 6.
Moerman, R., et al., A Coverslip Method for Controlled Parallel Sample Introduction into Arrays of (Sub)nanoliter Wells for Quantitative Analysis, Analytical Chemistry, Aug. 15, 2003, pp. 4132-4138, vol. 75, No. 16.
Monahan, J., et al., A Method for Filling Complex Polymeric Microfluidic Devices and Arrays, Analytical Chemistry, 2001, pp. 3193-3197, vol. 73.
Nagrath, S., et al., Isolation of rare circulating tumour cells in cancer patients by microchip technology, Nature, Dec. 2007, pp. 1235-1241, vol. 450.
Nilsson, J., et al., Review of cell and particle trapping in microfluidic systems, Analytica Chimica Acta, 2009, pp. 14-157, vol. 649.
Ostuni, E., et al., Selective Deposition of Proteins and Cells in Arrays of Microwells, Langmuir, 2001, pp. 2828-2834, vol. 17.
Patankar, N.A., Hydrophobicity of Surfaces with Cavities: Making Hydrophobic Substrates from Hydrophilic Materials?, Journal of Adhesion Science and Technology, 2009, pp. 413-433, vol. 23.

(56) References Cited

OTHER PUBLICATIONS

Qin, D., et al., Soft lithography for micro- and nanoscale patterning, Protocol, 2010, pp. 491-502, vol. 5, No. 3.
Quere, D., Wetting and Roughness, Annu. Rev. Mater. Res., 2008, pp. 71-99, vol. 38.
The University of North Carolina at Chapel Hill, Australian Application No. 2013267227, Examination Report No. 2, dated Feb. 7, 2017.
The University of North Carolina at Chapel Hill, Australian Application No. 2013267227, Notice of Acceptance, dated Feb. 20, 2017.
The University of North Carolina at Chapel Hill, European Application No. 13796502.6, Extended European Search Report, dated Nov. 20, 2015.
The University of North Carolina at Chapel Hill, European Application No. 13796502.6, Office Action, dated Jan. 16, 2017.
The University of North Carolina At Chapel Hill, European Application No. 13796502.6, Office Action, dated Sep. 12, 2018.
The University of North Carolina At Chapel Hill, European Application No. 13796502.6, Office Action, dated Oct. 30, 2019.
The University of North Carolina at Chapel Hill, European Patent Application No. 13796502.6, Office Action, dated Nov. 17, 2017.
The University of North Carolina at Chapel Hill, International Application No. PCT/US2013/043562, International Search Report, dated Sep. 3, 2013.
The University of North Carolina at Chapel Hill, International Application No. PCT/US2013/043562, International Preliminary Report on Patentability, dated Dec. 2, 2014.
The University of North Carolina at Chapel Hill, Japanese Patent Application No. 2015-515226, Official Action, dated May 30, 2017.
The University of North Carolina at Chapel Hill, Japanese Patent Application No. 2015-515226, Examiner's Decision of Rejection, dated Feb. 20, 2018. cited by applicant.
U.S. Appl. No. 14/404,225, Office Action, dated Jun. 15, 2017.
U.S. Appl. No. 14/404,225, Final Office Action, dated Oct. 27, 2016.
U.S. Appl. No. 14/404,225, Office Action, dated Jan. 4, 2016.
Vulto, P., et al., Phaseguides: a paradigm shift in microfluidic priming and emptying, Lab on a Chip, May 7, 2011, pp. 1561-1700, vol. 11, No. 9.
Waltermo, A., et al., Foam Films and Surface Force Studies of Aqueous Solutions of Octyl-.beta.-Glucoside, Journal of Dispersion Science and Technology, 1994, pp. 273-296, vol. 15, No. 3.
Wang et al., Dissolution-guided wetting for microarray and microfluidic devices, Lab on a Chip, Jul. 20, 2012, vol. 12, No. 17.
Wang et al., Systematic prevention of bubble formation and accumulation for long-term culture of pancreatic islet cells in microfluidic device, Biomedical Microdevices, Jan. 18, 2012, vol. 14, No. 2.
Wang, Y., et al., Broadening Cell Selection Criteria with Micropallet Arrays of Adherent Cells, Cytometry Part A, 2007, pp. 866-874, vol. 71 A.
Wang, Y., et al., Micromolded arrays for separation of adherent cells, Lab on a Chip, 2010, pp. 2917-2924, vol. 10.
Wang, Y., et al., Micropatterning of Living Cells on a Heterogeneously Wetted Surface, Langmuir, 2006, pp. 8257-8262, vol. 22.
Wang, Y., et al., Stability of Virtual Air Walls on Micropallet Arrays, Analytical Chemistry, 2007, pp. 7104-7109, vol. 79.
Wood, D.K., et al., Single cell trapping and DNA damage analysis using microwell arrays, PNAS, Jun. 1, 2010, pp. 10008-10013, vol. 107, No. 22.
Y. Wang et al., Lab Chip, 2011, 11, 3089-3097 (2011).
Zahn, J.D., et al., Micromixing Within Microfluidic Devices, Methods in Bioengineering: Biomicrofabrication and Biomicrofluidics, 2009, pp. 59-85.
Zheng, W., et al., A simple PDMS-based microfluidic channel design that removes bubbles for longterm on-chip culture of mammalian cells, Lab on a Chip, 2010, pp. 2906-2910, vol. 10.
Decision to Grant corresponding to European Patent Application No. 13796502.6 dated Jun. 19, 2020.

* cited by examiner

C. 25% glucose deposited on Native, hydrophobic PDMS

B. 25% glucose deposited on oxidized, hydrophilic PDMS

A. Shape of sacrificial residue depends on contact angle during drying in microcavities

DISSOLUTION GUIDED WETTING OF STRUCTURED SURFACES

CROSS-REFERENCES

This application is a continuation application of U.S. patent application Ser. No. 15/995,360, filed Jun. 1, 2018, which is a continuation application of U.S. patent application Ser. No. 14/404,225, filed Nov. 26, 2014, now U.S. Pat. No. 9,994,805, which was filed under the provisions of 35 US.C. § 371 and claims the priority of International Patent Application No. PCT/US2013/043562, filed May 31, 2013, which is related to U.S. provisional application No. 61/653,783, filed May 31, 2012, the contents of all of which are incorporated herein by reference in their entirety.

STATEMENT OF GOVERNMENT SUPPORT

This invention was made with government support under Grant Numbers EB012549 and HG004843 awarded by the National Institutes of Health. The government has certain rights in the invention.

FIELD OF THE INVENTION

The present invention concerns microfabricated devices and methods of wetting gas-entrapping features therein.

BACKGROUND OF THE INVENTION

Lab-on-a-chip technology has made rapid progress for applications in cell biology and biochemical assay.[1] Lab-on-a-chip systems that enable the efficient performance of assays with low reagent consumption typically contain features on the structured surfaces of the microfabricated devices such as microfluidic chips and microwell arrays where air bubbles can be easily trapped upon the addition of a solvent or solution. The trapped air bubbles result in Cassie-state wetting on the surface. This wetting phenomenon has been exploited for specific applications, such as selective deposition of proteins and cells to the areas that are in contact with the aqueous solution, for example, on the surface between microwells (but not inside microwells),[7] or on the top surface of micropallets (but not in the space among micropallets).[8] Nevertheless, for a majority of applications, the trapped air bubbles in microfabricated devices are an obstacle in the use of the device and the air bubbles need to be removed to allow the entire surface to be in full contact with solutions of analytes, cell-culture medium, or other fluids.[9, 10]

Microwell arrays, useful platforms for cell culture and assays at single-cell resolution, are examples of microfabricated devices possessing gas-entrapping features.[2, 11] Since microwell arrays are often made from polymers, such as PDMS, which are either hydrophobic or only slightly hydrophilic in their native form, trapping of air bubbles inside the microwells are encountered whenever the array is covered with an aqueous solution. To solve this problem, plasma treatment is generally used to make the surface hydrophilic; however, in many of the common polymers this hydrophilization is only temporary, and either a partial or complete hydrophobic recovery is usually observed.[14, 15] In addition to surface oxidation, several methods are currently used for removing trapped air bubbles in cavities, including vacuum application, pressurization, centrifugation, vibration and sonication.[10, 16-18] Alternatively, low surface tension liquids (e.g. ethanol, $\gamma=22.4$ mN·m$^{-1}$ can be used to initially wet the surface prior to exchange with water ($\gamma=72.9$ mN·m$^{-1}$) or an aqueous buffer.[19, 20] Besides microwell arrays, corners and dead ends in microfluidic channels have similar problems with surface wetting and bubble formation. A new microfluidic design, called a phaseguide, based on a stepwise advancement of the liquid-air interface using the meniscus pinning effect, can effectively eliminate the probability of trapping air bubbles in complex microfluidic geometries such as corners and deep angular structures.[6] However, this method is difficult to remove trapped air in microcavities microwells, or dead ends, since it relies on the creation of strips of material on the wall along the direction of advancing fluid.

Although all of the above methods are effective in preventing or removing air bubbles in specific cases, there remains a need for a simpler, passive method for preventing the formation of gas bubbles or removing gas bubbles from microfabricated devices having microcavities, corners, dead ends and other gas-entrapping features.

SUMMARY OF THE INVENTION

A first aspect of the invention is a microfabricated device (e.g., a microwell array, a microfluidic device) having at least one gas-entrapping feature on a structured surface formed therein that entraps gas bubbles which prevent the wetting of said feature with a solvent or solution. The device includes a sacrificial residue in contact with said gas entrapping feature. The nature of the sacrificial residue may be either hydrophilic or hydrophobic, and may be either a solid or a combination of a solute and solvent suitable for the gas-entrapping feature to be wetted.

In some embodiments, the gas-entrapping feature comprises a microwell, corner, microcavity, dead end, post, trap, hole, passage, channel, or combination thereof.

In some embodiments, the surface of the gas entrapping feature is oxidized (e.g., plasma oxidized).

A further aspect of the invention is a method of wetting a microfabricated device while inhibiting the entrapment of gas bubbles therein, comprising: (a) providing a microfabricated device as described herein, (b) treating the microfabricated device by priming with a sacrificial residue in contact with the gas-entrapping features, and then (c) treating said microfabricated device with a solvent or solution sufficient to dissolve and remove said sacrificial residue from said gas-entrapping feature while concurrently wetting said gas-entrapping feature with said solvent or solution.

The foregoing and other objects and aspects of the present invention are explained in greater detail in the drawings herein and the specification set forth below. The disclosures of all United States patent references cited herein are incorporated by reference herein in their entirety.

The volumetric concentration of glucose was varied as shown in the figure. SEM images were obtained at a tilt angle of 30°.

Figure 3:
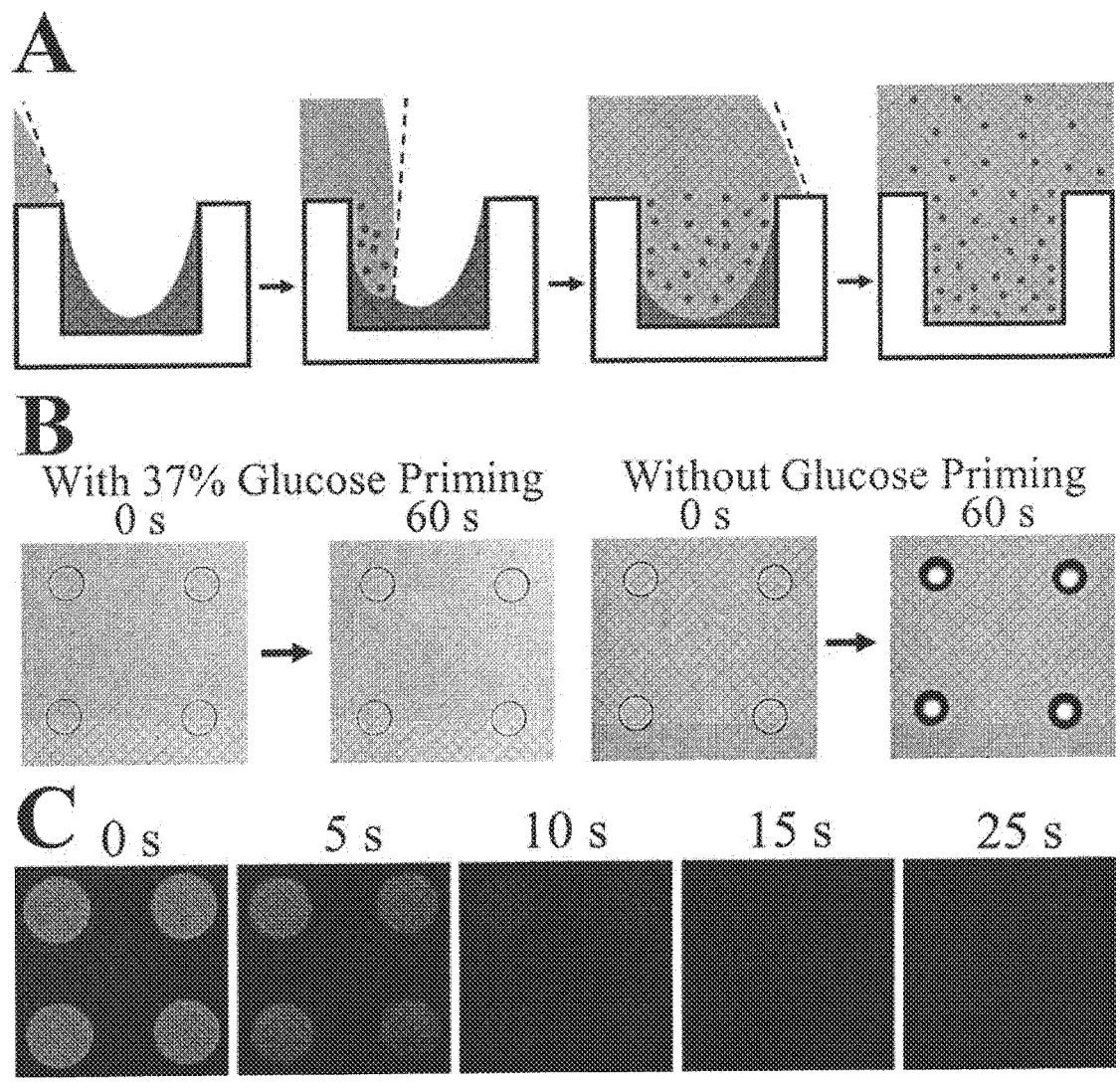

FIG. 3. Dissolution guided wetting in microwells. (A) Schematic showing the wetting process on a microwell guided by dissolution of glucose. (B) Wetting in PDMS microwells (D=50 µm, H=55 µm) with 37% glucose priming (left panel) and without glucose priming (right panel). Prior to wetting, PDMS samples were treated with air plasma for 2 min., primed with 37% glucose (or not primed), and stored at room temperature in air for one month. (C) Time-lapse fluorescence images showing the dissolution of glucose (mixed with 200 µg/mL TRITC dextran) in a microwell array (D=200 µm, H=55 µm).

Figure 4:
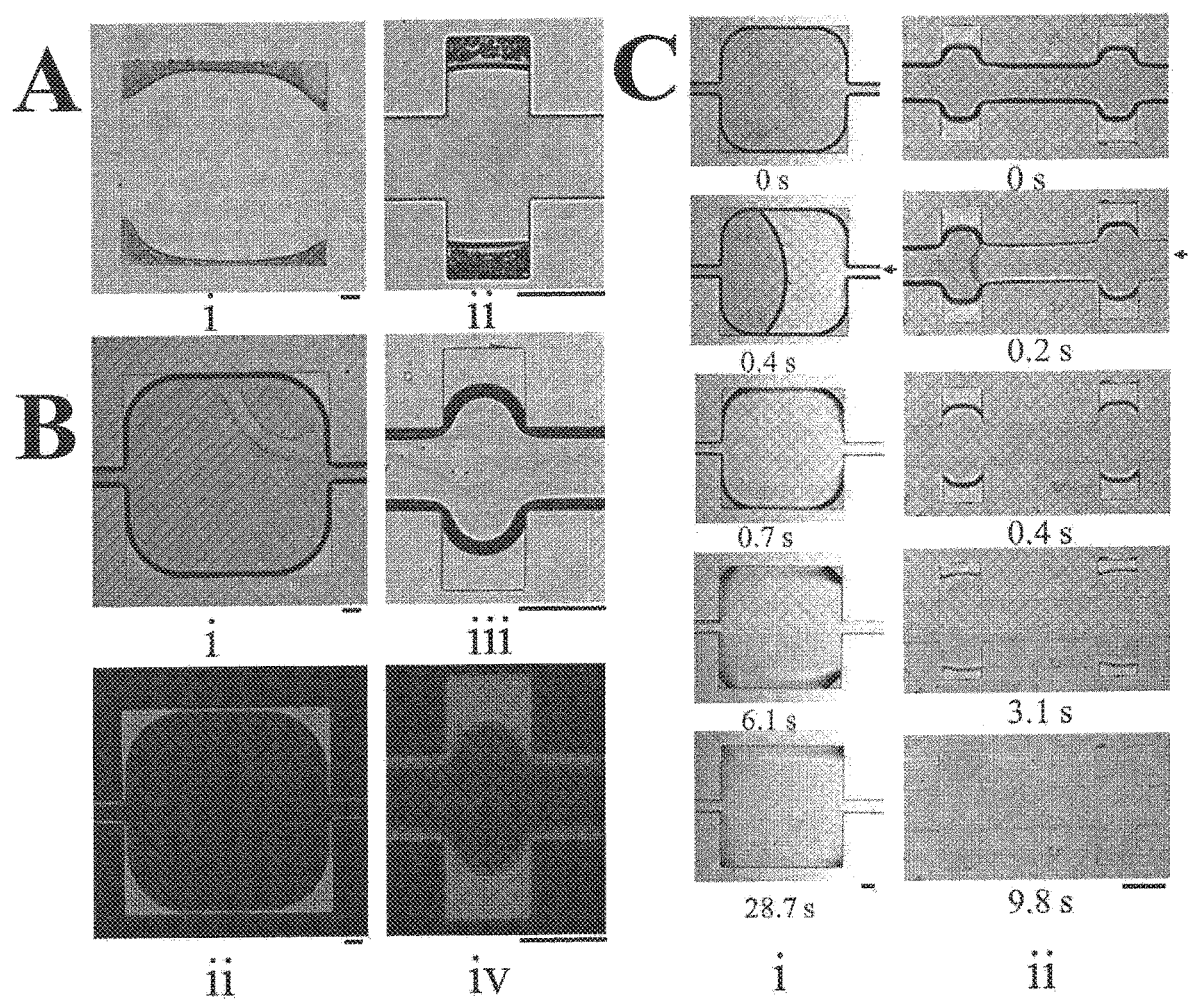

FIG. 4. Dissolution guided wetting in corners and dead ends of microfluidic channels. (A) Air bubble entrapment was present in corners (i) and dead ends (ii) of PDMS microfluidic channels on day 7 after bonding. (B) Priming the corners (i, ii) with glucose, and dead ends (iii, iv) with sorbitol. Transmitted light (i and iii) and fluorescence (ii and vi) images clearly show the corners and dead ends were occupied with sugar. The sugar was mixed with 200 µg/mL TRITC dextran for fluorescence imaging. (C) Time-lapse transmitted light images showing the dissolution of glucose in corners (i) and sorbitol in dead ends (ii). Arrows indicate the direction of water flow. Prior to test, the channels were stored at room temperature in air for one week. Scale bar=50 µm.

Figure 5:
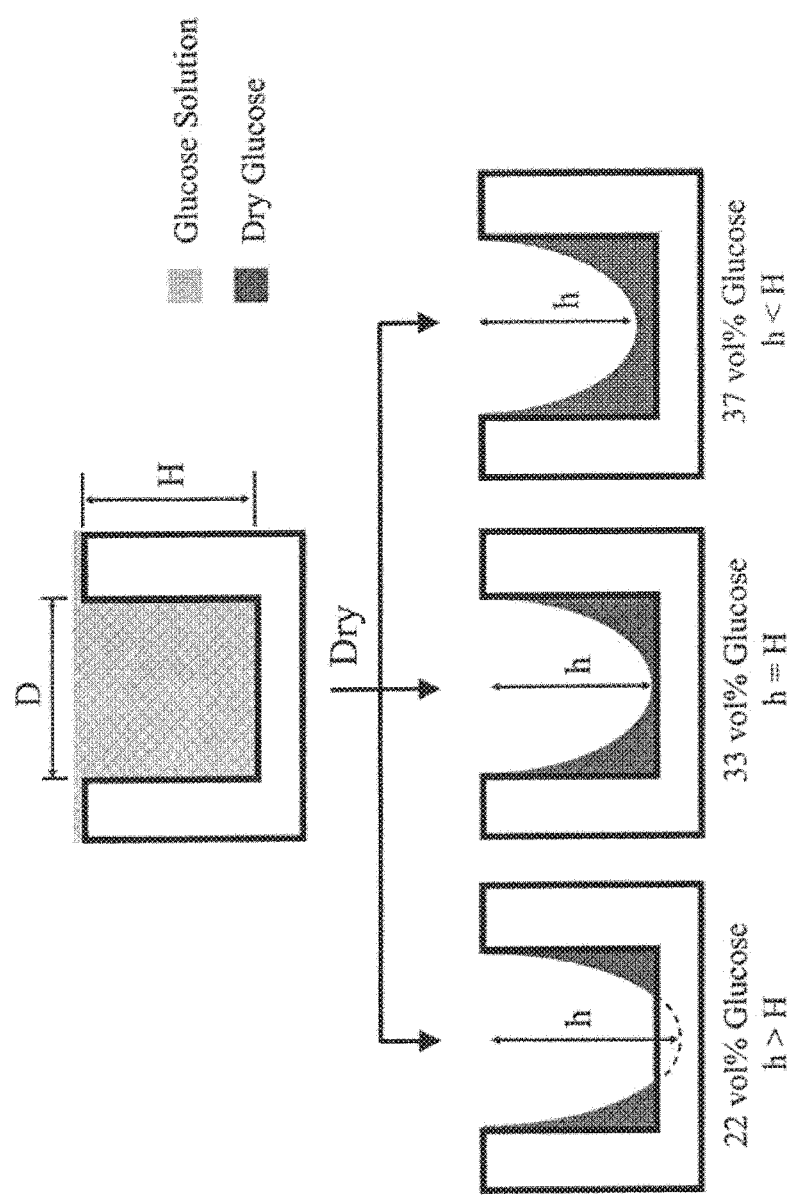

FIG. 5. Schematic showing that the drying of glucose solution in a microwell results in a conformal, elliptical, cone-shaped coating of solid glucose. The degree of coverage depends on the concentration of glucose.

Figure 6A:
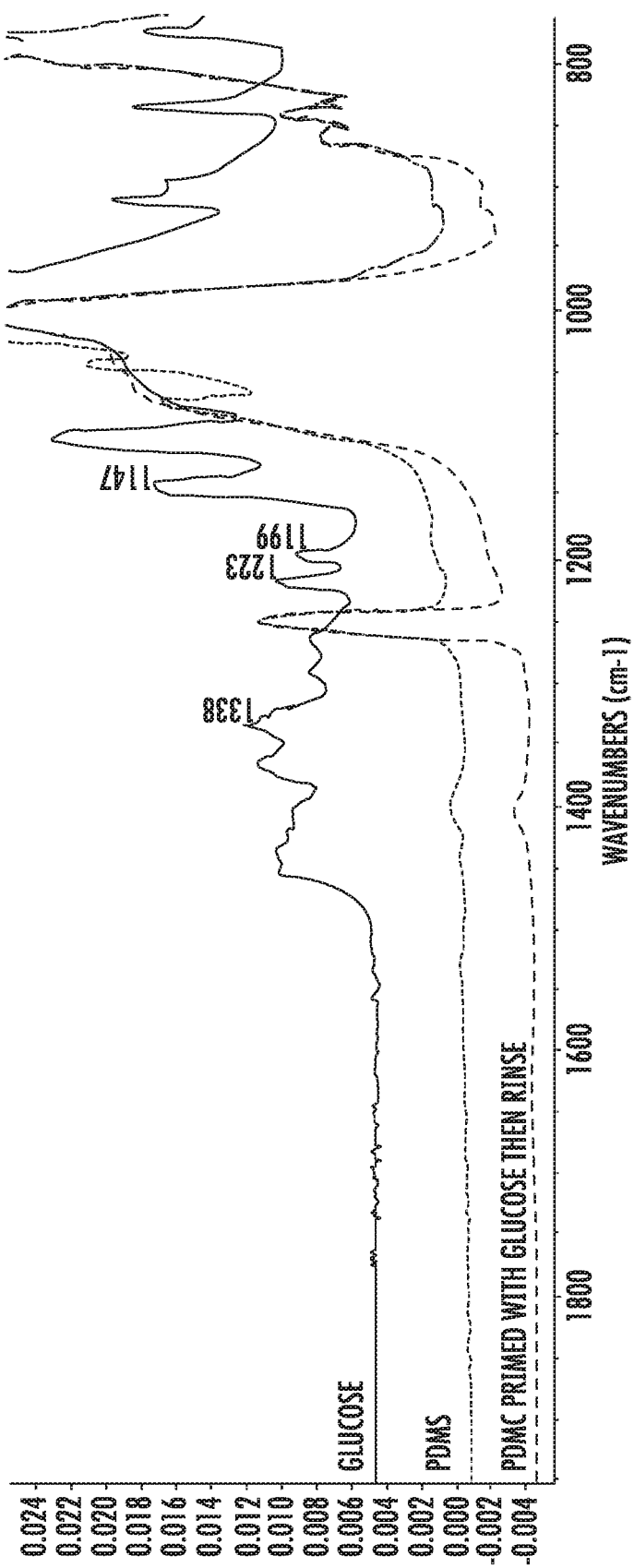
Figure 6B:
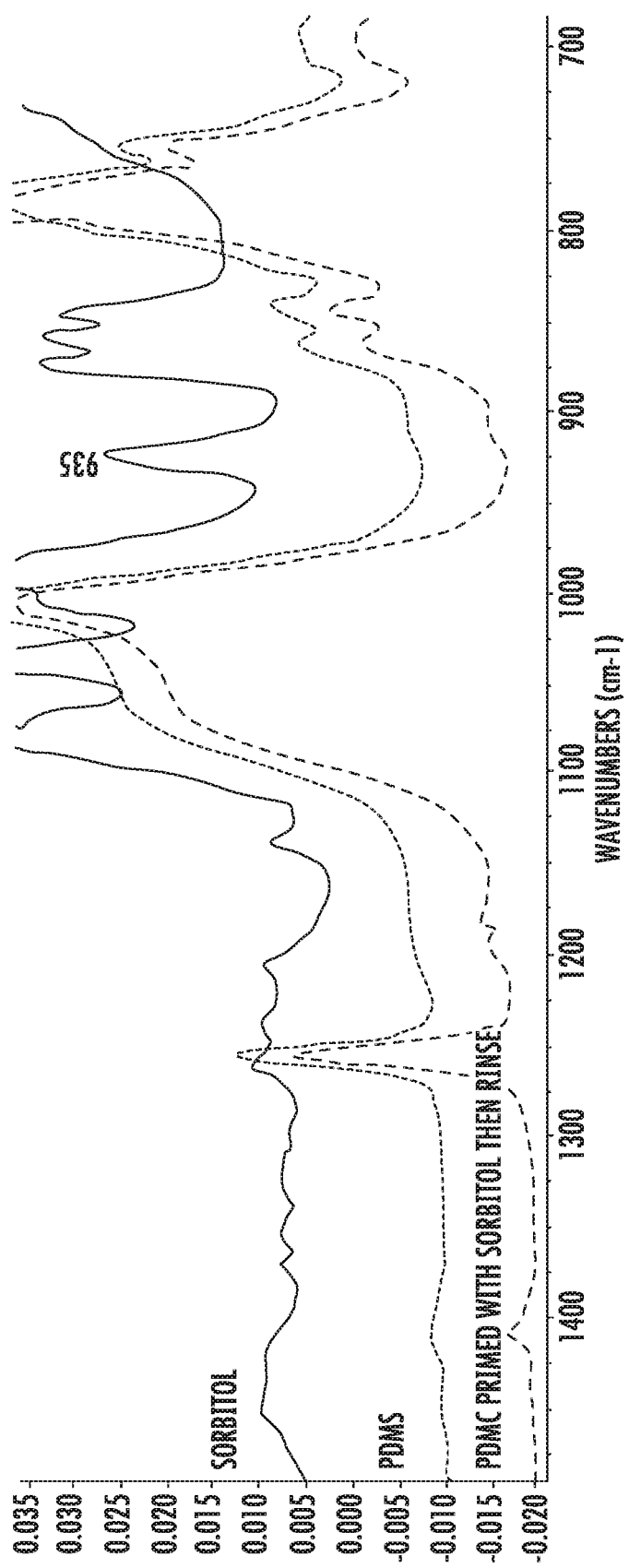

FIGS. 6A and 6B. ATR-FTI R spectra of PDMS samples primed with glucose (FIG. 6A) and sorbitol (FIG. 6B) then rinsed with water. A native PDMS sample was used as a negative control, and glucose and sorbitol were used as positive controls.

Figure 7:
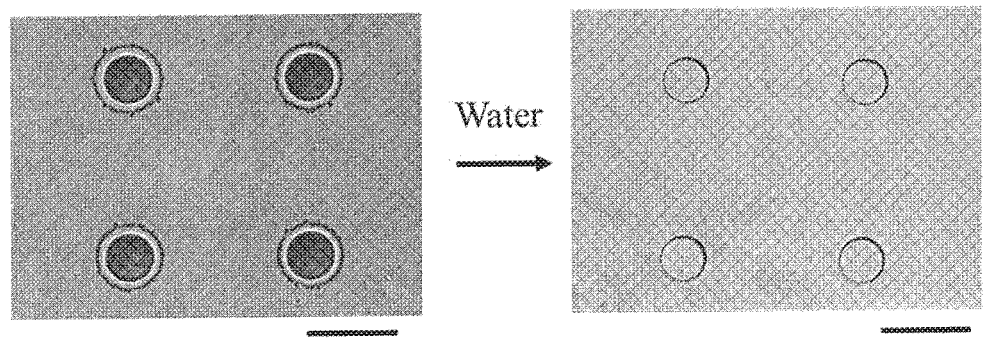
Figure 8:
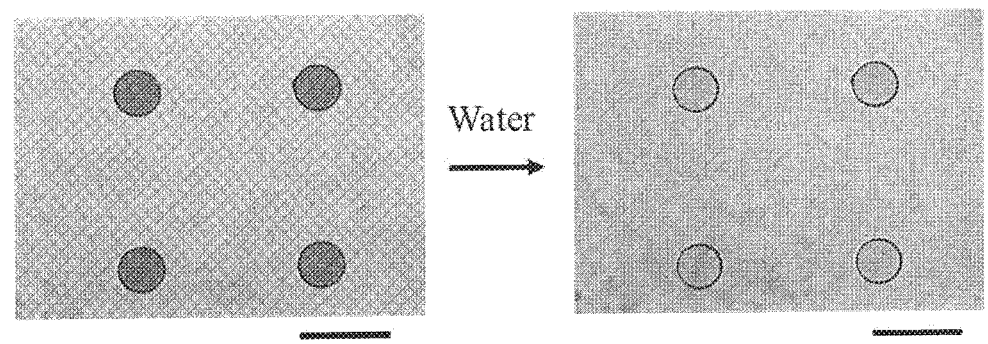

FIG. 7. Transmitted light images showing glucose guided wetting in microwells formed in polystyrene. Scale bar=100 µm FIG. 8. Transmitted light images showing sorbitol guided wetting in PDMS microwells. Scale bar=100 µm.

Figure 9:
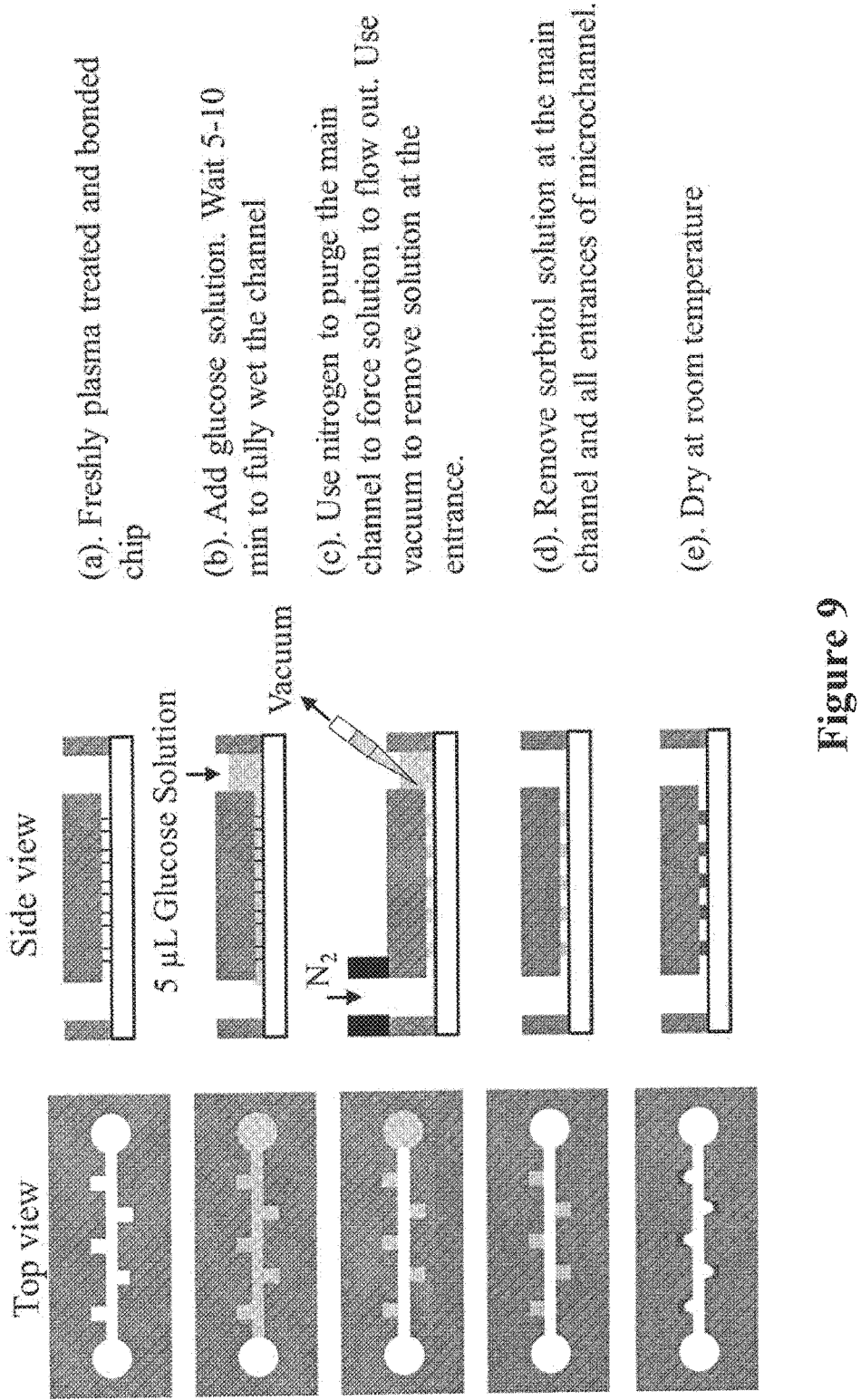

FIG. 9. Process of priming the corners and dead ends of microfluidic channels with a 30 vol % glucose solution or a 50 vol % sorbitol solution.

Figure 10:
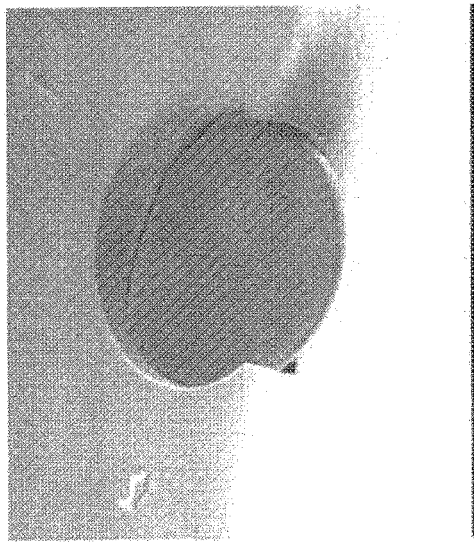
Figure 10:
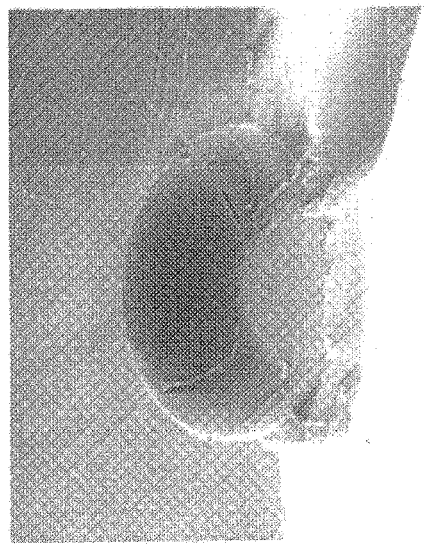
Figure 10:
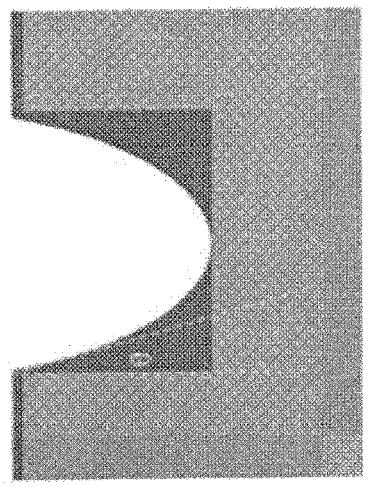

FIG. 10. Shape of glucose residue in PDMS microwells is dependent on the interfacial property of PDMS/glucose solution. (A) Schematic showing the wetting of glucose solution in a PDMS microwell upon drying. The contact angle θ determines the shape of glucose. (B) A parabolic residue of glucose is formed on an oxidized, hydrophilic PDMS. (C) A flat, column shaped residue of glucose is formed on a native, hydrophobic PDMS.

Figure 11:
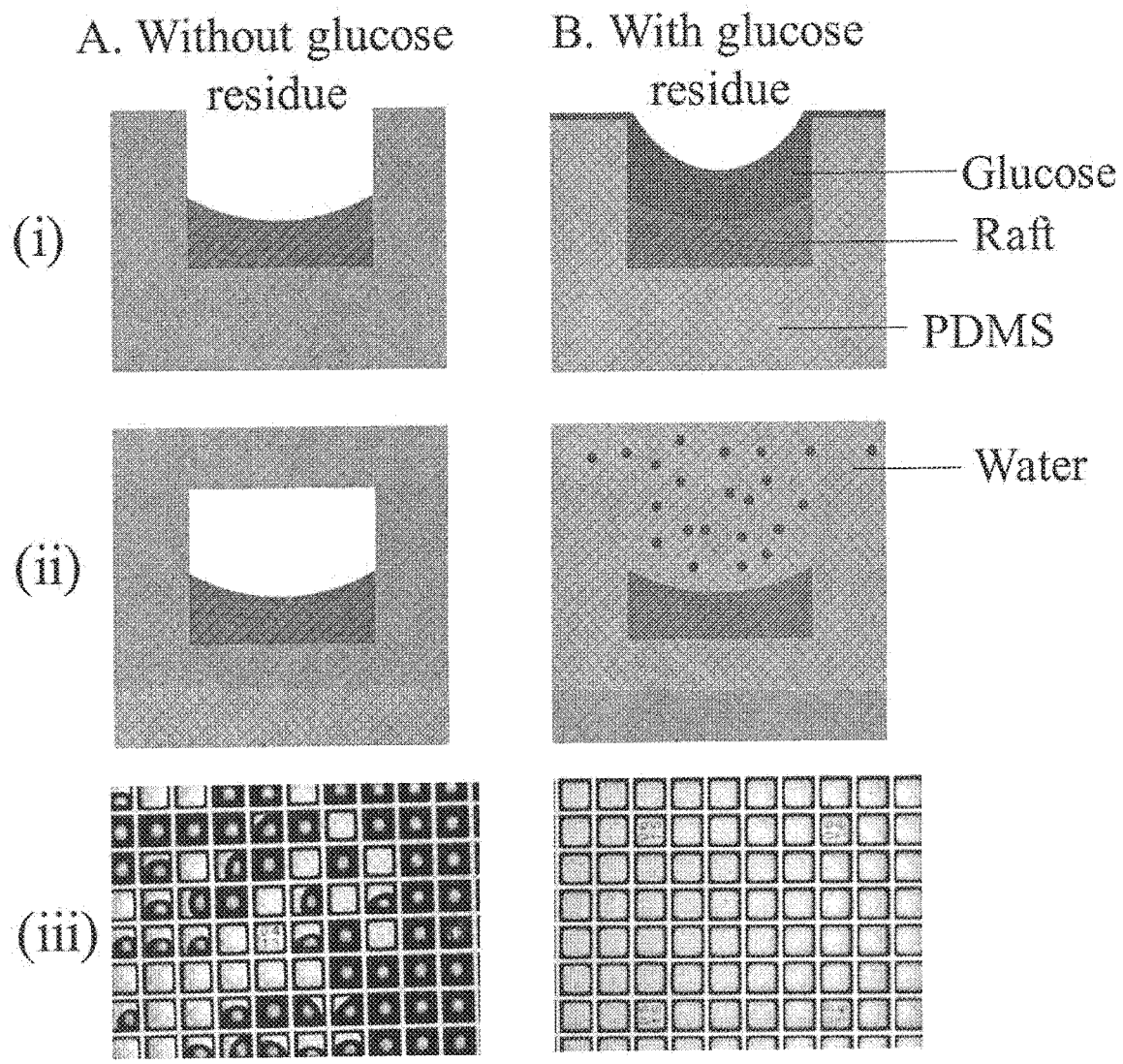

FIG. 11. Wetting of microraft array without (A) and with (B) deposition of glucose residue. (i) Schemes of cross-sectional view of a raft. (ii) Schemes of wetting on a raft. (iii) Transmitted light images showing wetting on a raft array. Each well has a dimension of 200 µm×200 µm×100 µm (length×width×height). To deposit glucose residue on the array, a 40 wt % glucose solution was applied on the raft array followed by aspiration to remove excess solution and drying in air.

DETAILED DESCRIPTION OF THE PREFERRED EMBODIMENTS

The present invention is now described more fully hereinafter with reference to the accompanying drawings, in which embodiments of the invention are shown. This invention may, however, be embodied in many different forms and should not be construed as limited to the embodiments set forth herein; rather these embodiments are provided so that this disclosure will be thorough and complete and will fully convey the scope of the invention to those skilled in the art.

Like numbers refer to like elements throughout. In the figures, the thickness of certain lines, layers, components, elements or features may be exaggerated for clarity. Where used, broken lines illustrate optional features or operations unless specified otherwise.

The terminology used herein is for the purpose of describing particular embodiments only and is not intended to be limiting of the invention. As used herein, the singular forms "a," "an" and "the" are intended to include plural forms as well, unless the context clearly indicates otherwise. It will be further understood that the terms "comprises" or "comprising," when used in this specification, specify the presence of stated features, integers, steps, operations, elements components and/or groups or combinations thereof, but do not preclude the presence or addition of one or more other features, integers, steps, operations, elements, components and/or groups or combinations thereof.

As used herein, the term "and/or" includes any and all possible combinations or one or more of the associated listed items, as well as the lack of combinations when interpreted in the alternative ("or").

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and claims and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting" or "in contact" with, etc., another element, it can be directly on, attached to, connected to, coupled with and/or contacting the other element or intervening elements can also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature can have portions that overlap or underlie the adjacent feature.

Spatially relative terms, such as "under," "below," "lower," "over," "upper" and the like, may be used herein for ease of description to describe an element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus the exemplary term "under" can encompass both an orientation of over and under. The device may otherwise be oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only, unless specifically indicated otherwise.

It will be understood that, although the terms first, second, etc., may be used herein to describe various elements, components, regions, layers and/or sections, these elements, components, regions, layers and/or sections should not be limited by these terms. Rather, these terms are only used to distinguish one element, component, region, layer and/or section, from another element, component, region, layer and/or section. Thus, a first element, component, region, layer or section discussed herein could be termed a second element, component, region, layer or section without departing from the teachings of the present invention. The sequence of operations (or steps) is not limited to the order presented in the claims or figures unless specifically indicated otherwise.

Devices of the present invention are, in general, microfabricated devices such as microwell arrays and microfluidic devices formed from or in a selected substrate. Such devices are known and examples include, but are not limited to, those described in U.S. Pat. Nos. 7,927,830; 7,775,088; 7,742,662; 7,556,776; 7,169,577; 7,161,356; 6,670,133; and 6,632,655. In some embodiments, the microfabricated devices have one or more fluid passages, chambers, channels, wells, conduits or the like that are configured to contain microvolumes of liquids, typically wherein one or more of the dimensions is less than 500 µm. In some embodiments, the device further comprises a main channel in fluid communication with the gas-entrapping feature; wherein the surface of said main channel is substantially free of the sacrificial residue. In some embodiments, the device comprises a microfluidic network, with the gas-entrapping feature comprising a first region of the microfluidic network.

Devices of the invention can be formed from any suitable substrate material including but are not limited to silica based substrates, such as glass, quartz, silicon or polysilicon, as well as other substrate materials, such as gallium arsenide and the like. Other suitable materials include but are not limited to polymeric materials, e.g., plastics, such as polymethylmethacrylate (PMMA), polycarbonate, polytetrafluoroethylene (e.g., TEFLON™) polyvinylchloride (PVC), polydimethylsiloxane (PDMS), polysulfone, polystyrene, polycarbonate, polyimide, cyclic-olefin copolymer, polymethylpentene, polypropylene, polyethylene, polyvinylidine fluoride, acrylonitrile-butadiene-styrene copolymer (ABS), and the like, as well as polymerized photoresists, e.g., SU-8, 1002F and the like (see, e.g., U.S. Pat. No. 6,103,446).

Substrate materials are often selected based upon their compatibility with known techniques, such as microfabrication. Suitable substrate materials are also generally selected for their compatibility with the full range of conditions to which the microfabricated. devices may be exposed, including extremes of pH, temperature, salt concentration, and application of electric fields. Accordingly, the substrate material may include materials normally associated with the semiconductor industry. In the case of semiconductive materials, it will often be desirable to provide an insulating coating or layer, e.g., silicon oxide, over the substrate material, and particularly in those applications where electric fields are to be applied to the device or its contents. In some embodiments, the substrates used to make the mircofabricated device are silica-based, more preferably glass or quartz, due to their inertness to the conditions described above, as well as the ease with which they are microfabricated in other embodiments polymeric substrate materials are preferred for their ease of manufacture, low cost and disposability, as well as their general inertness to most extreme reaction conditions. These polymeric materials may include treated surfaces, e.g., derivatized or coated surfaces, to enhance their utility in the microfluidic system, e.g., provided enhanced fluid direction, e.g., as described in U.S. Pat. No. 5,885,470, and which is incorporated herein by reference in its entirety for all purposes. In other embodiments the microfabricated device is made using a combination of materials, such as silica-based and polymeric materials.

The material of the microfabricated device may be opaque, translucent or transparent. The device can be formed of a single layer substrate of a single material or a laminated or multi-layer configuration of the same or different material substrates. The device may be a single layer monolithic substrate or (more typically) a multiple layer device (e.g., having two or three layers or more) and having a thickness that is between about 0.2 mm to about 15 mm. The thickness of the device is not critical, as the thickness of top and bottom parts of the device are not critical, so long as the proper inner chamber dimensions are provided for the intended use. The device can comprise a bioactive agent that is formed in a matrix of the substrate and/or applied or coated on a primary surface thereof to define one or more analytical sites on the device for analysis and/or to define a barrier zone.

Microfabricated devices of the invention can be made by any suitable technique including but not limited to microfabrication techniques such as photolithography, wet chemical etching, laser ablation, reactive ion etching (RIF), air abrasion techniques, injection molding, LIGA methods, metal electroforming, embossing, and other techniques. Suitable techniques may also be those employed in the semiconductor industry. Other suitable techniques include but are not limited to molding techniques, such as injection molding, embossing or stamping, or by polymerizing the polymeric precursor material within the mold (See U.S. Pat. No. 5,512,131).

Microfabricated devices may have either hydrophobic or hydrophilic surfaces. Further, hydrophobic surfaces can be made hydrophilic by treatment with air or oxygen plasma, chemical surface modification, or physical surface deposition. For example, PDMS is a hydrophobic material and its hydrophobic surface can be made hydrophilic by oxygen plasma treatment (See Bodas D. and Khan-Malek, C. Microelectronic Engineering, 2006, 83, 1277-1279), or by chemical grafting of a thin hydrophilic poly(acrylic acid) on a hydrophobic PDMS surface (See U.S. Pat. No. 6,596,346 and Analytical Chemistry, 2002, 74, 4117-41.23); or by physical deposition of a glass layer (See Abate, A. et al., Lab Chip, 2008, 8, 516-518).

Microfabricated devices frequently contain gas-entrapping features such as microcavities, dead ends, corners, posts, holes, channels, traps, and passages. As used herein, gas refers to any substance in the gaseous phase and may include nitrogen, oxygen, carbon dioxide, or mixtures such as air.

The microfabricated devices are primed with a sacrificial residue that is suitable for dissolution guided wetting of the gas-entrapping features and therefore remove or-prevent the formation of gas bubbles in the device. For microfabricated devices that use solvents or solutions that are aqueous, the sacrificial residue may be comprised of any suitable material, including but not limited to salts, carbohydrates (e.g., monosaccharide, disaccharide, oligosaccharide, or polysaccharide), and other hydrophilic polymers. Particular examples include, but are not limited to, sodium chloride, dextran, polyethylene glycol, poly(acrylic acid), poly(4-vinylpyridine), poly(vinyl alcohol), dextran, alginate, agarose, chitosan, cellulose, glucose, sucrose and sorbitol. In some embodiments, the sacrificial residue is comprised of a non-metabolizable sugar (e.g., sorbitol, xylitol or mannitol, etc.). When using a salt as the sacrificial residue, a salt that is readily dissolved in an aqueous solution may be used. Non-limiting examples of such a salt are sodium chloride, potassium chloride, sodium sulfate, sodium bisulfate, sodium phosphate, monosodium phosphate, disodium phosphate, potassium phosphate, monopotassium phosphate, dipotassium phosphate, calcium chloride, magnesium chloride, or a combination thereof. The sacrificial residue is, in some embodiments, amorphous. When a microfabricated device uses a solvent or solution that is non-aqueous, then a suitable material that is hydrophobic should be chosen for the sacrificial residue. Such suitable hydrophobic materials are hydrophobic polymers, low molecular weight organic solids, non-volatile liquids. Particular examples of hydrophobic polymers include, but are not limited to, polyethylene, polypropylene, polyvinyl chloride, polystyrene, nylons, polyesters, acrylics, polyurethane, and polycarbonates, polylactic acid, poly(lactic-co-glycolic acid), poly(methyl methacrylate). Particular examples of low molecular weight organic solids include, but are not limited to, paraffin wax, naphthalene, anthracene, aspirin (acetylsalicylic acid), 2-naphthol, fat. Particular examples of non-volatile liquids include, but are not limited to, synthetic oils (for example mineral oil), vegetable oils (for example olive oil), lipids, silicone oil, liquid epoxy resin.

The sacrificial residue may be applied by any suitable technique. In one embodiment, the sacrificial residue is a suitable solute that is dissolved in an aqueous or non-aqueous solvent, contacting the selected solution comprising the solvent and solute with the gas-entrapping feature to be primed, and allowing the solution to dry thereon thereby depositing the solute in contact with the gas-entrapping feature. In another embodiment, a material for the sacrificial residue may be dispersed, rather than dissolved, in a suitable aqueous or non-aqueous solvent. In yet another embodiment, the sacrificial layer is comprised of a solid material that may be brought into contact with a gas-entrapping feature as a fine particulate dust and/or by melting the solid at a suitable temperature.

It is noted that the sacrificial residue used to achieve dissolution guided wetting of the structured surface does not chemically modify the surface. While plasma oxidation of the PDMS surface can be used in certain embodiments, this step to modify the surface is not required as the application of vacuum or solvents with the appropriate characteristics could be used to provide Wenzel-state wetting of the structured surface in the deposition of the sacrificial residue in contact with gas-entrapping features.

Once prepared, the primed microfabricated devices may be packaged in a water-proof container, and/or packaged in a container with a desiccant, for subsequent use.

In use, the primed microfabricated devices are typically rinsed, depending on its intended purpose, with an aqueous or non-aqueous rinse solution for a time, in an amount and at a temperature sufficient to dissolve and remove the sacrificial residue from said gas entrapping feature, and preferably while concurrently wetting said gas entrapping feature with said rinse solution. The device may then be rinsed with a second aqueous or non-aqueous solution. (e.g., a growth media, an assay or reagent media, a reaction media, etc.) to remove the previous rinse solution therefrom and ready the device for its intended purpose.

The present invention is explained in greater detail in the following non-limiting examples.

A method is described to prevent or eliminate gas bubbles on structured surfaces of microfabricated devices possessing microcavities, corners, dead ends and other gas-entrapping features. In one example, a microfabricated device was made using PDMS. The process for priming the microfabricated device for dissolution guided wetting of gas-entrapping features was composed of two steps: the surface was first made hydrophilic by plasma treatment, then primed with an aqueous monosaccharide solution, and placed in dry storage. Prior to use of the microfabricated device, the end user simply adds water to dissolve a monosaccharide followed by rinsing to remove any trace of the monosaccharide in the microfabricated device or in solution. The dissolution of the monosaccharide guides a complete wetting of the gas-entrapping features, leaving the structured surfaces free of gas bubbles. Microwells and microfluidic channels made from PDMS were used as the model to demonstrate this dissolution-guided wetting of the gas-entrapping features.

Materials used were D-glucose, D-sorbitol, phosphate buffered saline (PBS) tablets, tetramethylrhodamine isothiocyanate-dextran (TRITC-dextran, average molecular weight 500,000), and octyltrichlorosilane were purchased from Sigma Aldrich (St. Louis, Mo.). SU-8 photoresist was purchased from MicroChem Corp. (Newton, Mass.). PDMS was prepared from the Sylgard 184 silicone elastomer kit (Dow Corning, Midland, Mich.).

PDMS, a polymer known to have a rapid and complete hydrophobic recovery,[15] was selected as the material to create the structured surfaces of the microwells and microfluidic channels. Microwell arrays and microfluidic channels were fabricated by micromolding PDMS on an SU-8 master by conventional soft lithography.[21] The SU-8 master was fabricated by standard photolithography on a glass slide spin-coated with an SU-8 layer of 55 µm thickness.[22] The master mold was treated with 50 µL, oetyltrichlorosilane in a vapor-phase silanization process in a polycarbonate desiccator (Fisher Scientific): the desiccator was degassed by an oil-free pump for 2 min and then closed for 16 h. PDMS prepolymer (10:1 mixture of base: curing-agent in the Sylgard 184 kit) was spread on the master mold and degassed under vacuum to remove air bubbles from the polymer. The master was baked at 100° C. on a hotplate for 30 min to cure the PDMS. The PDMS forming the microwell arrays or microchannels was then obtained by peeling it from the master. For microwell arrays, the depth of the microwells was 55 µm, and the diameter was in the range from 10 µm to 3 mm. For microfluidic channels, holes of 2-mm diameter were first punched at the ends of the patterns on PDMS to serve as solution reservoirs. The PDMS and a glass slide were treated in an air-plasma cleaner (Harrick Plasma, Ithaca, N.Y.) for 2 min before they were sealed to form an enclosed microfluidic channel.

The degree of wetting of the gas-entrapping features was determined by measuring the water contact angle. The water contact angle was measured with a pocket Goniometer PG-3 (Fibro system AB, Sweden) using a 5 µL drop of deionized water. The contact angle was measured at 5 s after the drop was applied. An average of 10 measurements was calculated per surface.

Microwells were primed with glucose as the sacrificial residue. Glucose solutions in water of different volumetric concentrations (0%, 22%, 30%, and 37%) were prepared. The volumetric concentration of glucose was calculated from its weight concentration by assuming the volume of solution is the sum of the volumes of the solute and solvent.

PDMS microwell arrays were first treated in an air-plasma for 2 min to generate hydrophilic surfaces by oxidation. An open chamber was created surrounding the array using a self-sealing, square PDMS ring (25×2.5×6 mm) attached to the substrate. An aqueous solution of glucose (1-2 mL) was added to the chamber to wet the array surface. The array was tilted, and the excess solution was removed by aspirating with a-pipet attached to a vacuum hose and liquid trap. By evaporating the remaining water at room temperature in air, solid glucose was deposited in the. microwells. The microwells primed with glucose were observed with. a Nikon Eclipse TE300 inverted, fluorescence microscope and by scanning electron microscopy (SEM) (FEI Quanta 200 ESEM, FEI Company).

FIG. 9 shows the protocol for priming the corners and dead ends of microfluidic channels. Immediately after plasma treatment and bonding on glass, 5 μL of the solution was added to one entrance of the microfluidic channel. Due to the hydrophilic surface of the freshly plasma-bonded PDMS, the solution spontaneously wet the entire channel within a few minutes, even in the corners and dead ends without any trapped air bubble. A hose supplied with nitrogen was placed on the other entrance of the microfluidic channel to purge the main channel, so that the solution in the main channel was expelled leaving residual sugar solution in the corners and dead ends. The solution flushed into the reservoir was removed by aspiration. A drop of water was added to the entrance while the main channel was being. purged with nitrogen. The water diluted the expelled sugar solution at the entrance and was quickly aspirated, which serves to prevent the possibility of dried sugar solution blocking the main channel. After priming, the devices were stored at room temperature. The sugar solution trapped in corners and dead ends within the device was allowed to gradually dry over 1-2 days by evaporation. A 30 vol % glucose solution was used to fill the corners in a microfluidic channel. A 50 vol % sorbitol solution was used to fill the dead ends in a microfluidic channel where sorbitol was found to be more effective due to the higher solubility of sorbitol in water.

The wetting behavior (complete wetting, partial wetting, or non-wetting) of PDMS microwell arrays and microfluidic channels, either primed with glucose or not, was determined by adding water and observing the presence of trapped air bubbles under microscope. Air bubbles in the microwells and microfluidic channels were readily discerned by brightfield microscopy by virtue of a thick dark boundary being formed between air and PDMS due to differences in the refractive indices of water (1.33), PDMS (1.43)[23] and air (1.00),[7] Similarly, deposition of glucose in the microwells and microfluidic channels could be ascertained due to refractive index mismatches of air (1.00), PDMS (1.43) and glucose (1.51).[24] To observe the dissolution process of glucose by fluorescence microsocopy, the glucose solution was mixed with 200. μg/mL TRITC-dextran and used to prime microwells and microfluidic channels. The microwells and microfluidic channels were imaged using the Nikon Eclipse TE300 microscope equipped with a CY3 filter set (0-2E; Nikon Instruments; excitation filter 528-553 nm dichroic 565 nm long pass, emission 590-650 nm). Time lapse images were collected with a cooled CCD camera (Photometrix Cool Snap; Roper Scientific, Tucson, Ariz.) using NIS-Elements software.

Air bubbles are often trapped in microfabricated devices. For a majority of biological applications, full wetting of microwells, i.e. Wenzel wetting state, without entrapment of air bubbles is often a requirement. Since many polymers (such as PDMS) used for these microfabricated devices are hydrophobic, entrapment of air within the hydrophobic microwell cavity is a frequent: occurrence unless additional steps are taken[7] To prevent air bubble formation, plasma treatment, either oxygen or air, is often used to render the microwell surface hydrophilic and permit instantaneous aqueous wetting (FIG. 1A).[25] However, for many polymers, the surface recovers its hydrophobic state quickly after oxidation so that the devices cannot be re-wetted after long-term storage without re-oxidation of the device.[26] Among ten different polymers of interest air microfabrication, PDMS has the most rapid hydrophobic recovery.[15] In the current studies, the water-droplet contact angle on PDMS films immediately after plasma treatment was $10°±5°$, but recovered to $42°±8°$ (n=3) after 3 days. The microwell array could be fully wetted on day 0, but by day 3 air bubbles were trapped inside small microwells (diameter D=50 μm, height H=55 μm, FIG. 1A) upon addition of water. The water-droplet contact angle on the PDMS surface continued to increase over time to $65°±11°$ (n=3) at day 6 with entrapment of air bubbles even in large microwells (D=100 μm, H=55 μm, FIG. 1A). A similar trend was observed for microwells made from other polymers, such polystyrene, poly(D,L-lactide) and SU-8 epoxy photoresist, although these exhibited a slower hydrophobic recovery than PDMS. These observations are consistent with a recent report which tested hydrophobic recovery of 10 common polymers.[15]

The stability or duration of air trapping inside the wells was also dependent on the hydrophobicity of the PDMS. When the contact angle recovered to $42°±8°$ (n=3) at day 3, the air bubbles persisted for approximately 10 min inside the microwells (D=50 μm, H=55 μm) before displacement by water. When the contact angle recovered to $75°±5°$ (n=3) at day 14, the air bubbles were stably trapped in the microwells for >4 hours (D=50 μm, H=55 μm). For hydrophilic materials (contact angle <90°) with cavities, trapping of air is thought to be possible—since the cavities can provide an energy barrier to stop the water from entering—them, Wenzel-state wetting is thermodynamically favorable for hydrophilic materials (contact angle <90°) with cavities,[27] but this energy barrier may be adequate to prevent, at least temporarily, the transition from a Cassie state to a Wenzel state. For example, as previously reported, air can be trapped in spherical cavities 400-800 nm in diameter on hydrophilic gold surfaces (contact angle=700°.[28]

Figure 1:
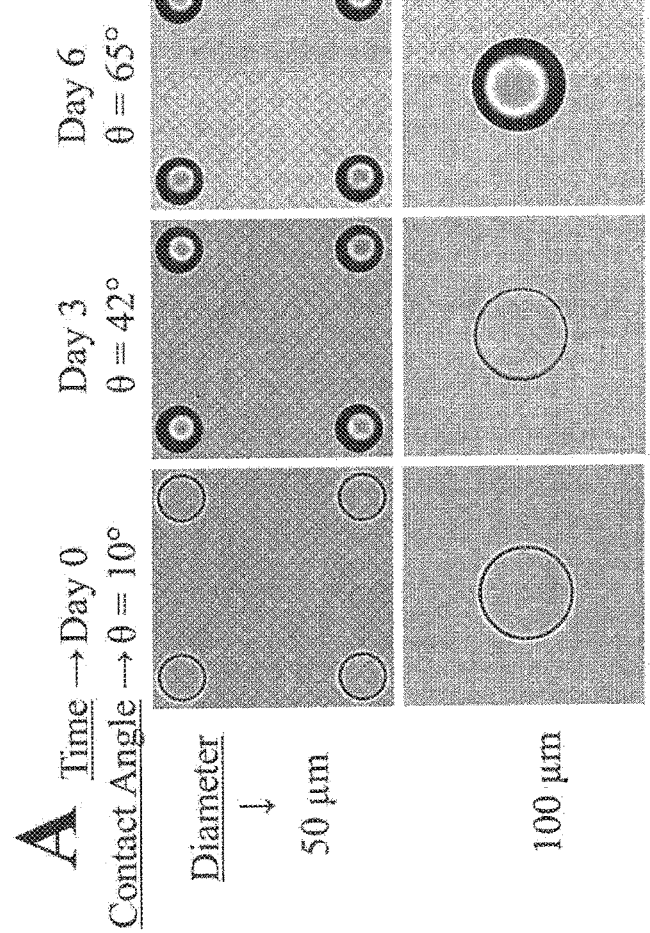
FIG. 1. Wetting of PDMS microwells. (A) Brightfield images of PDMS microwells (H=55 µm, D=50 and 100 µm) placed in an aqueous solution at day 0, day 3 and day 6 after plasma treatment. Air bubble entrapment was present on day 3 (50 µm) and day 6 (100 µm). (B) Schematic showing the wetting of microwells. $\phi$ is defined as the angle that a diagonal through the well makes with the well's base and top edge of its side wall and $\theta$ is the angle of the aqueous solution on the side wall of the cavity.
Figure 1:
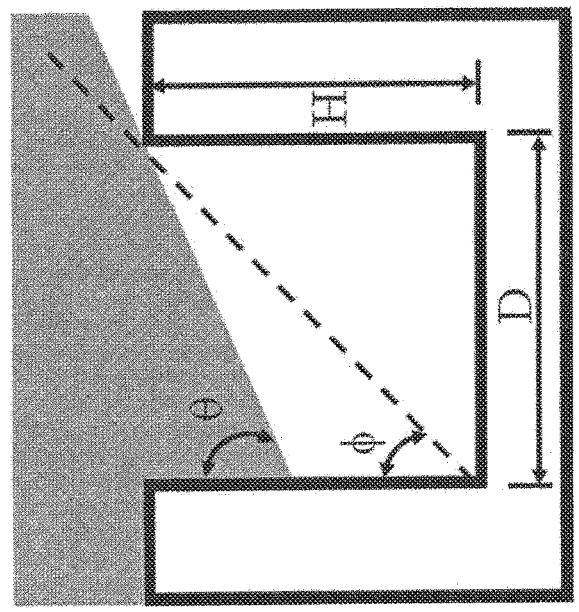

The trapping of air bubbles inside microwells can be explained by the scheme shown in FIG. 1B where is defined as the angle that a diagonal through the well makes with the well side wall and θ is the angle of the aqueous solution on the side wall of the cavity. For a hydrophilic surface, such, as freshly oxidized PDMS, θ<φ, the advancing liquid can wet the vertical wall and bottom before reaching the other edge of the well. As a result, air can be pushed out from the well resulting in a. homogeneous wetting (Wenzel state). For a hydrophobic surface, θ<φ, advancing liquid reaches the other edge of the well before it can wet the side and bottom walls (FIG. 1B). As a result, air can be trapped inside the well resulting in heterogeneous wetting (Cassie state). Wetting of a rough solid surface with a liquid has been extensively studied with theoretical models, although the exact mechanism of air entrapment has not been elucidated.[29, 30, 31, 32]

Figure 2:
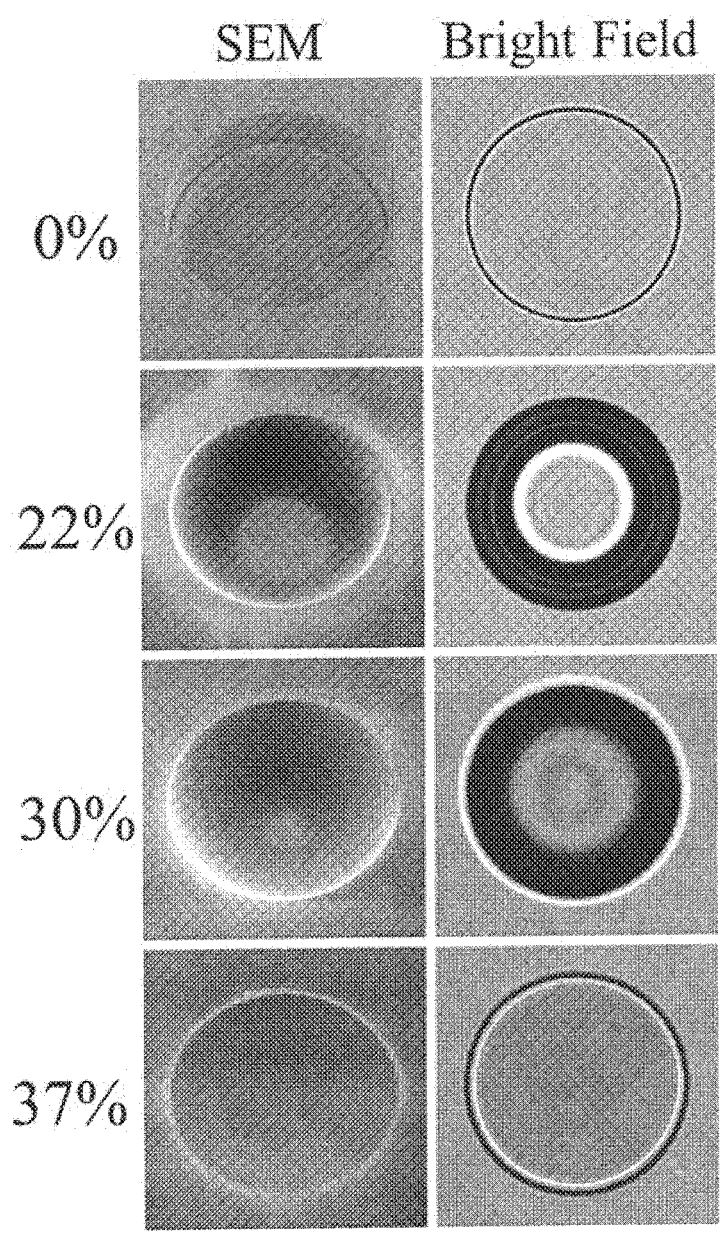
FIG. 2. Priming the hydrophilic microwells with glucose. SEM and brightfield images showing a microwell (D=200 µm, H=55 µm) filled with a glucose solution and then dried.

The priming of hydrophilic microwells with glucose can prevent the trapping of air bubbles in microcavities through dissolution guided wetting eliminates a significant annoyance in the use of microwell arrays for a standard biology lab. Typically, end users prefer to have devices in a ready-to-use state without the need for pre-processing immediately prior to the biological application. In the case of microwell arrays, a fully wettable surface without the need for plasma oxidation, high vacuum exposure, or pre-treatment with a toxic, low-viscosity liquid such as ethanol would facilitate their use and acceptance. The priming of gas-entrapping features with glucose, as one example of a sacrificial residue, achieves the goal of providing a microfabricated device that could be stored for long periods, yet remain fully wettable. PDMS microwells were first oxidized with air plasma to generate a hydrophilic surface. A solution of water-soluble material was added to the microwells forming Wenzel-state wetting on the surface. Excess liquid was removed by aspiration. Upon drying, a conformal coating of solid material was generated inside the microwells. Water (or a suitable aqueous solution) could then fully wet the primed microwells at a later time by dissolving the sacrificial residue of glucose inside the microwells, thus preventing or eliminating air bubbles in the microcavities. Although many water soluble materials are available, a preferred embodiment uses non-toxic, biocompatible materials with fast dissolution rates in water. Phosphate buffered saline (PBS), a common salt solution used in biology, may also be used but care should be taken to avoid the formation of large salt crystals formed in the wells that can pop out of place instead of a conformal coating on the well walls. Solid sugar polyols, such as D-glucose and D-sorbitol, are preferred materials for the sacrificial residue as they rapidly dissolve in water and are biocompatible. In one embodiment, a PDMS microwell array was wetted with an aqueous glucose solution (37% volumetric concentration) and the excess volume above the wells was then removed. After solvent evaporation, a conformal coating of solid glucose lined the microwell walls and floor (FIG. 2). For the microwells primed with glucose at a concentration of 30%, the glucose layer appeared to coat only a portion of the microwell walls and floor (FIG. 2). Lower glucose concentrations (22%) resulted in even lower coverage of the microwell surface. The angle of the glucose layer on the side wall was also steeper at the lower glucose concentrations. This observation is consistent with the theoretical calculation by assuming that the contour of the dried glucose layer is regarded as elliptical in shape. The relative coverage of dry glucose in the microwell is dependent only on the concentration of glucose c, not on the dimension of microcavities (diameter and height). Therefore, when using glucose as the sacrificial residue to prime the microcavities a preferred embodiment is to use a glucose solution with c>33%, for a structured surface possessing microcavities with a wide range of sizes (10 μm-3 μm) and depths.

The glucose coating alters both θ for the side wall and for the well, which facilities the rewetting of the microwells by water. Since water can rapidly dissolve glucose, its dissolution guides the rewetting of the microwells (FIG. 3A), To determine if the change in θ and φ for the glucose-coated wells could result in microwell wetting, PDMS microwell arrays (D=50 μm, H=55 μn) were tested one month after oxidation and priming with a 37% or 0% glucose solution. FIG. 3B shows the wetting on PDMS microwells with glucose priming (left panel) and without glucose priming (right panel). For microwells without glucose priming, air bubbles formed in microwells. For microwells primed with a 37% glucose solution, no air bubbles formed. This anti-bubble function was effective for 4 months, the longest storage time tested to date, suggesting that the changes in θ and φ were successful in maintaining wettability over time.

To visualize the rate of glucose dissolution, a fluorescently doped glucose solution (37% glucose with 200 μg/mL TRITC-dextran, 0.5 MD) was used to prime a PDMS microwell array (microwells with D=200 μm, H=55 μm) one month prior to the experiment. The loss of fluorescence in the well was then tracked over time to follow glucose dissolution. After addition of water, the microwells were observed to completely wet followed by a loss of the priming layer over a time period of 25 s (FIG. 3A, C). Following wetting of the well's top surface, dissolution of glucose guides the filling of the well with the aqueous solution. Video examination showed the difference in the wetting characteristics of microwells with and without glucose coating.

A source of the change in θ is the presence of the glucose coating which creates a hydrophilic sacrificial residue in contact with the gas-entrapping features of the PDMS microfabricated device such that the water rapidly and entirely wets the structured surface of the device. However, it is possible that the glucose layer also prevents the hydrophobic recovery of the PDMS, thus facilitating the spread of the aqueous solution into the cavity near the edges of the glucose layer. To determine whether a glucose layer could maintain the hydrophilicity of the plasma-treated PDMS surface, the contact angle of PDMS films was evaluated at varying times after priming with glucose. PDMS films were oxidized with plasma and primed with 37% or 0% glucose solutions spread over the surface and dried in air. The films were then stored in air for 0, 2, 5, or 12 days (n=3 for each condition and time). Immediately prior to measurement of the water-droplet contact angle, the arrays were rinsed with water and dried under a nitrogen stream, and the contact angle was measured. An attenuated total reflectance (ATR)-FTIR spectrometer (Nicolet iSIO, Thermo Scientific) was used to confirm the absence of glucose residue on the PDMS surfaces (FIG. 6). At day 0, the contact angle for both primed and unprimed PDMS films was 10°±5°. By day 2, the contact angle for glucose-primed and unprimed PDMS films was 49°±2° and 41°−±6°, respectively. At day 5, the angle was 56°±4° for a primed film and 63$^{-°}$±6° for an unprimed film. At day 12, the angle was 65°±8° for a primed film and 72°±4° for an unprimed film. These results demonstrated that the glucose priming did not significantly delay hydrophobic recovery of the underlying PDMS structured surface. The initial change in θ<φ created by the glucose layer enabled wetting of the upper cavity surface while the subsequent dissolution of glucose ensured that the entire PDMS microcavity could be filled with the aqueous solution. This method for preventing bubble entrapment functioned equally well for microwells made from other materials such as polystyrene (FIG. 7). Sorbitol was also tested as a sacrificial residue for priming PDMS microwells and results similar to those shown above were obtained (FIG. 8).

Similar to microwell arrays, air bubbles can be trapped in corners and dead ends of microfluidic channels (FIG. 4A). To demonstrate the dissolution guided wetting in the corners and dead ends of microfluidic channels, microfluidic devices were built by molding PDMS channels from a master and then bonding it with glass slides through plasma oxidation. Immediately after bonding the channel was primed with glucose or sorbitol solution. Due to the hydrophilic nature of the freshly oxidized PDMS surface, both the sugar solutions wet the entire channel quickly, even in corners and dead ends. The sugar solution was removed by purging the channel with nitrogen and aspiration from the reservoir. After purging, residual sugar solution remained trapped in the corners and dead ends. A 30% glucose solution was used to prime the corners, and a 50% sorbitol solution was used to prime dead ends. The higher solubility of sorbitol (59.6 vol %) over glucose (37.1 vol %) was found to be preferred for the dead ends used in these studies due to the small volumes trapped in these structures. Upon drying, residual solid sugar remained in the corners and dead ends (FIG. 4B). The priming of solid sugars is expected to survive for prolonged times due to their non-volatility, and their stability in a wide range of temperature due to their high melting point (146° C. for glucose and 95° C. for sorbitol). After storing the devices at room temperature for 7 days, water was introduced into the channels (FIG. 4C). For the device studying air trapping in corners, water passing through the channel dissolved the glucose in the corners over a 30 s time period. The dissolution of glucose was seen to guide the wetting of the corners in a manner similar to that seen in the microwells. A similar observation was made for the sorbitol-primed dead ends. Due to relatively smaller dimension (50×50 μm for the dead end) compared to corners (500 μm square), the dissolution was faster (~10 s). Air bubble entrapment was not observed in the primed devices, but was present in identical unprimed devices.

The coverage of glucose priming in a microwell may be estimated by the concentration of the glucose solution used. Assuming the height of the liquid layer above the rim of the microwell was negligible, the total volume of glucose solution loaded into each microwell was:

$$V_1 = \frac{\partial D^2 H}{4} \quad (1)$$

where D is the diameter of the well and H is its height. During evaporation of the aqueous solvent, the glucose solution did not dewet from the freshly plasma-oxidized, hydrophilic surface. Consequently a conformal coating formed lining the inside of the microwells. If the contour of the glucose layer is regarded as elliptical in shape, the volume of empty space in the well that is not occupied by solid glucose is:

$$V_2 = \frac{\partial D^2 h}{6} \quad (2)$$

where h is the height of microwell above solid glucose. If the volumetric concentration of glucose is c, then $$cV_1 = V_1 - V_2 \quad (3)$$

Thus $$\frac{h}{H} = \frac{3(1-c)}{2} \quad (4)$$

When c>0.33, then h<H, which means the well is fully covered with glucose. When c 0.33, then h>H, which means the well is only partially covered with glucose (FIG. 5). The images are consistent with theoretical prediction that the concentration of the glucose solution may be modified in order to generate full coverage of the interior surface of the microwells. Based on equation (4), the relative coverage (h/H) is dependent only on the concentration of glucose c, not on the dimension of microcavities (D and H). Therefore, in one embodiment, the microcavities of a microfabricated device can be fully primed by using a glucose solution with c>33%, even for a surface possessing microcavities with a wide range of sizes (10 μm-3 mm) and depths.

As described above, glucose and sorbitol were used. as a sacrificial residue for guiding wetting of water (or aqueous solution) in microcavities, corners and dead ends. After wetting, it is desirable to completely remove glucose and sorbitol from the chips without any residue left on the surface. Attenuated total reflection Fourier transform infrared (ATR-FTIR) spectroscopy is a surface-sensitive diagnostic technique which can detect a trance amount of molecules on the top surface (0.5-5 μm) of a sample. A flat PDMS sample was oxidized with plasma for 2 min and then primed with a thin layer of glucose or sorbitol in the same way as was used to prime microwell arrays. The PDMS sample was dried in air and stored at room temperature for 7 days. The coated PDMS sample was soaked in DI water for 5 min to dissolve glucose or sorbitol, rinsed with DI water ×5 times, and dried in air. The. PDMS sample was then characterized by an ATR-FTIR spectrometer (Nicolet iS10, Thermo Scientific) with a Zinc Selenide (ZnSe) crystal to detect the presence of glucose or sorbitol residue on the PDMS surfaces (FIG. 6). A native PDMS sample was used as a negative control, and glucose and sorbitol were used as positive controls. The characteristic peaks of glucose (1338, 1223, 1199 and 1147 $cm^{-1}$) and sorbitol (935 $cm^{-1}$) were absent on coated PDMS samples (after water rinse). The spectra of coated PDMS samples (after water rinse) were exactly same as the native PDMS sample. These results demonstrate that glucose and sorbitol residues on PDMS surface were not detectable. PDMS is well known to absorb small hydrophobic molecules such as rhodamine B and Nile red (M. Toepke and D. Beebe, *Lab Chip,* 2006, 6, 1484-1486 (2006)), Glucose and sorbitol are highly hydrophilic molecules (glucose has four hydroxyl groups and sorbitol has five hydroxyl groups) so that they are unlikely to be absorbed by PDMS. Glucose and sorbitol are neutral molecules without any charged and reactive functional groups, so that they are unlikely adsorbed on the PDMS surface via electrostatic or covalent interactions. Because no residue is left in chips, glucose and sorbitol are ideal sacrificial residues for guiding wetting of water (or aqueous solution) in microcavities, corners and dead ends.

In the above examples, glucose has been shown to be effective to cover the PDMS microcavities and guide their wetting. Among ten different polymers of interest for microfabrication, PDMS. has the most rapid hydrophobic recovery (V. Jokinen et al., *Biomicrofluidics,* 2012, 6, 016501 (2012)). Therefore, dissolution guided wetting using a glucose sacrificial residue on microwells made with other materials such as polystyrene should be as effective as, if not easier than, in PDMS. To demonstrate the glucose-guided wetting is applicable to microwells made from other materials, a microwell array was fabricated from polystyrene by our recently reported soft lithography micromolding technique (Y. Wang et al., *Lab Chip,* 2011, 11 3089-3097 (2011)), The wells had a diameter of 50 μm and a height of 55 μm. The polystyrene microwell array was oxidized with air plasma for 2 min, primed with a 37 vol % glucose solution in the same way as with microwell arrays formed from PDMS. After priming, the micro-wells were covered with glucose (FIG. 7). After storage at room temperature for 7 days, water was added to the polystyrene microwell array to test the rewetting guided by glucose. Water quickly (~20-30 s) and completely dissolved the glucose and no air bubbles were trapped in the microwells (FIG. 7). This result demonstrates that dissolution guided wetting using glucose as the sacrificial residue is applicable to microfabricated devices made from materials other than PDMS.

Since glucose is an energy source for microbial metabolism, end users may be concerned about bacterial or fungal contamination during storage, especially in a humid and non-sterile environment. This issue can be addressed by sterilization after the coating is applied using gamma-ray irradiation or ethylene oxide. Sugars that are poor energy sources such as sorbitol, xylitol or mannitol can also be used to replace glucose (K. Isotupa et al., *Am. J. Orthod Dentofac. Orthop.*, 107, 497-504 (1995)). Dissolution guided wetting using sorbitol as the sacrificial residue in PDMS microwells has been successfully achieved. The wells have a diameter of 50 μm and a height of 55 μm. The PDMS microwell array was oxidized with air plasma for 2 min, primed with a 40 vol % sorbitol solution and dried in air. After priming, the microwells were covered with sorbitol (FIG. S4). After storage at room temperature for 7 days, water was added to the PDMS microwell array to test the rewetting guided by sorbitol. Water quickly (~20-30 s) and completely dissolved the sorbitol and no air bubbles were trapped in the microwells (FIG. 7). This result demonstrates the sorbitol functions as effectively as glucose in guiding rewetting in microwells. An additional advantage of sorbitol over glucose is its high solubility in water. The solubility of sorbitol in water is 220 g/100 mL water (equivalent to 59.6 vol %, which is much higher than that of glucose (91 g/100 mL water, equivalent to 37.1 vol %). Sorbitol's higher solubility is useful in filling deep microcavities or to guide wetting in dead ends in microfluidic devices.

As described above, the dissolution guided wetting in the corners and dead ends of microfluidic channels was demonstrated using microfluidic chips built by molding PDMS channels from a master mold and then bonding it with glass slides through plasma oxidation (FIG. 1a). Immediately after plasma treatment and bonding, 5 μL of a monosaccharide solution (in some experiments, the monosaccharide was mixed with 200 μg/mL TRITC dextran) was added to one reservoir for the microfluidic channel (FIG. 1b). Due to the hydrophilic surface of the freshly plasma bonded PDMS, the solution spontaneously wet the entire channel within a few minutes, even in corners and dead ends without trapped air bubbles. A hose supplied with nitrogen was placed at the opposite reservoir and used to purge the main microfluidic channel (FIG. 1c). The solution flushed out at the reservoir was removed by aspiration. A drop of water was added to the reservoir of the main channel during purging to dilute the monosaccharide solution as it exited the channel. The fluid in the reservoir was quickly aspirated after purging. After purging, residual solution remained trapped in the dead ends (FIG. 1d). The chips were then stored at room temperature and the residual monosaccharide solution in the device was allowed to gradually dry by evaporation (FIG. 1e). In these experiments, a 30 vol. % glucose solution was used to fill the corners in a microfluidic channel and a 50 vol % sorbitol was used to fill the dead ends in a microfluidic channel.

In another embodiment, a sacrificial residue is applied in contact with gas-entrapping features on native, hydrophobic structured surfaces of a microfabricated device. The shape of the sacrificial residue deposited depends on the interfacial property of the structured surface and the solution comprising the sacrificial residue material (FIG. 10-A). In microcavities, a parabolic shaped residue is formed when the solution can wet the solid with small contact angle 74. On the other hand, a flat, column shape is formed when the solution cannot wet the solid with a large contact angle θ (in other words, the solution dewets on the structured surface).

In this embodiment, PDMS is used with a 25 wt % glucose aqueous solution as the examples for the substrate of a microfabricated device having a structured surface and glucose in solution as the sacrificial residue material, respectively.

The native PDMS surface is hydrophobic which tends to trap air bubbles in microcavities and other gas-entrapping features. The PDMS surface can be oxidized with plasma treatment to change its surface to be hydrophilic. A 25 wt % glucose solution is immediately added to the hydrophilic PDMS surface. Upon drying in air, glucose forms a parabolic shape in microcavities (FIG. 10-B), which can effectively guide wetting when water is added to the surface. The parabolic shape is caused by the hydrophilic PDMS surface, on which the glucose aqueous solution wets and forms a small contact angle ($\theta<90°$).

When PDMS is not oxidized, glucose forms a flat, column shape in PDMS microcavities (FIG. 10-C). This is caused by the hydrophobic PDMS surface, on which the glucose aqueous solution dewets and forms a large contact angle ($\theta>90°$). This flat, column shape is not effective in guiding wetting in microcavities.

By using an organic solvent or an organic/aqueous mixture as the solvent, a parabolic shape of sacrificial residue can be applied to a native, hydrophobic PDMS surface with microcavities. Examples of organic solvents that are compatible with PDMS are ethanol, isopropanol, dimethylformamide, gamma-butyrolactone (GBL), gamma-valerolactone, etc. Organic solvents have much lower surface tension than water (72.8 dynes/cm), for example, ethanol (22.4 dynes/cm), isopropanol (23.0 dynes/cm). As a result, these organic solvents can wet native PDMS (19.8 dynes/cm) and form a small contact angle. A suitable material for a sacrificial residue can be dissolved in the organic solvent or an organic/aqueous mixture, and then applied to the native PDMS surface with microcavities. Examples of solvent-sacrificial residue material pairs are: ethanol/water mixture (50/5 wt/wt)-glucose isopropanol-polyvinyl alcohol, GBL-polyethylene glycol.

In another embodiment, a sacrificial residue can be directly deposited on structured surfaces having gas-entrapping features by utilizing the liquid-solid phase transition of the material used to form the sacrificial residue. For example, sorbitol (Acros Organics #132731000) has a melting point of 95° to 99° C. Sorbitol was heated at 100° C. to become a low-viscous liquid, and then it was applied to surfaces on which microcavities were present. Air bubbles were removed by applying vacuum or pressure. Excess sorbitol liquid was removed by aspiration. The microcavities were filled with liquid sorbitol which solidified as the device cooled to room temperature. Upon subsequent wetting, the sorbitol residue effectively guided wetting in microcavities by dissolution without air bubble entrapment.

In a further embodiment, a microraft array such as is described in Allbritton et al., Array of Micromolded Structures for Sorting Adherent Cells PCT Application No. PCT/US2011/025018 filed Feb. 16, 2011, herein incorporated by reference, is composed of a large number of micron-scale elements made from rigid plastics such as polystyrene, termed rafts, positioned at the bottom of microwells made from polydimethylsiloxane (PDMS). The scheme for the microraft array is shown in FIG. 11-A-i. Within the array, the rafts serve as releasable culture sites for individual cells or colonies. Cells are plated on the array in the same manner as a Petri dish, and the cells remain positioned on specific rafts while in culture so that single cells can expand into clonal colonies. To isolate target cells, a needle is inserted through the PDMS to dislodge a raft and its attached cell(s). The cell(s) is then collected for expansion, or downstream analysis.

Air bubbles are presented when water (or aqueous buffer, medium) is added on the array. The trapping of air bubbles is caused by the hydrophobic surface of PDMS (FIG. 11-A.-ii). The array can be treated with plasma to change the PDMS surface to be temporarily hydrophilic, but the PDMS surface can quickly recover its native hydrophobic nature in a few days. For example, two weeks after plasma treatment, air bubbles are presented on the array when water is added (FIG. 11-A-iii). The air bubbles need to be removed since they prevent cells from settling into the wells and attaching to the rafts.

To prevent formation of air bubbles, glucose was used as a sacrificial material and was deposited on the microraft array by applying a 40 wt % glucose solution on the plasma-oxidized microraft array followed by aspiration to remove excess solution and drying in air (FIG. 2-B-i). The glucose coated raft, array can be stored under ambient conditions for at least weeks to months. Even after sufficient time (2 weeks after plasma treatment and deposition of glucose residue) for the PDMS to recover its hydrophobic surface, the dissolution of glucose effectively guided wetting in wells when water was added (FIG. 11-B-ii) as shown by complete absence of air bubbles on the array after water addition (FIG. 11-B-iii).

Glucose is nontoxic and serves as an energy source for cells. Glucose is one of the main components of cell culture medium, for example, Dulbecco's Modified. Eagle's Medium (DMEM) has a. glucose concentration of 4.5 grams/liter. Glucose is perhaps one of the safest sacrificial residues to guide wetting in microfabricated devices used for applications involving biological cells. Glucose does not stay on the PDMS surface after rinsing with water as verified by attenuated total reflectance (ATR) FTIR spectroscopy. To demonstrate the lack of a detrimental effect of a glucose sacrificial residue on cell culture, a microraft array prepared with a glucose sacrificial residue as described above was rinsed with phosphate buffered saline (PBS) three times, then plated with 111299 cells, a human non-small cell lung carcinoma cell line. The proliferation and morphology of cells was normal and identical to those of cells cultured on a microraft array without glucose sacrificial residue. This result demonstrated that the glucose residue had no negative effect on the growth and health of the cultured cells.

A simple method has been described herein that prevents or eliminates the formation of gas bubbles in gas-entrapping features of microfabricated devices, thus solving a common problem encountered when fluids are added to such devices for a variety of lab-on-a-chip applications. The method involves priming the structured surfaces of the microfabricated device through the application of a sacrificial residue that achieves the dissolution guided wetting of the gas-entrapping features upon introduction of a suitable fluid for the intended use of the device. Microfabricated devices thus primed can be kept in dry storage for a prolonged period without loss of efficacy of the dissolution guided wetting. Gas bubble formation was prevented by simply adding a suitable solvent or solution to the device to dissolve the sacrificial residue. Simple, robust, and easily implemented methods such as this are needed to increase the rate of adoption of microwell arrays and microfluidic technologies in everyday laboratory practice as well as in the field and in clinical applications. The current technique represents an example of combining robust simplicity with functionality. If a sacrificial residue is selected that can act as an energy source for microbial metabolism, concerns about bacterial or fungal contamination during storage can be addressed by sterilization of the primed microfabricated device using gamma-ray irradiation or ethylene oxide. Sugars that are poor energy sources such as sorbitol, xylitol. or mannitol can also be used to replace. glucose.[33] Dissolution guided wetting can also be achieved with microfabricated devices having hydrophobic structured surfaces by selecting hydrophobic solvents and suitable solutes as the sacrificial residue. The method is applicable to a variety of polymer-based, lab-on-a-chip products with gas-entrapping features including microwell arrays and enclosed microfluidic systems where surface wetting is particularly challenging.

The foregoing description and embodiments is illustrative of the present invention, and is not to be construed as limiting thereof. The invention is defined by the following claims, with equivalents of the claims to be included therein.

REFERENCES

1. M. Kovarik et al., *Anal. Chem.*, 2012, 84, 516-540.
2. M. Charnley et al., *Integr. Biol.*, 2009, 1, 625-634.
3. S. Nagrath et al., *Nature*, 2007, 450, 1235411210.
4. Y. Wang et al., *Cytom. Part A*, 2007, 71A, 866-874.
5. J. Nilsson. et al., *Anal. Chim, Acta*, 2009, 649, 141-157.
6. P. Vulto et al, *Lab Chip*, 2011, 11, 1596-1602.
7. E. Ostuni. et al., *Langrnuir*, 2001, 17, 2828-2834.
8, Y. Wang et al., *Langrnuir*, 2006, 22, 8257-8262,
9. L. Hackett, Removing bubbles from small cavities, U.S. Pat. No. 5,368,634, 1994.
10. J. Monahan et al., *Anal. Chem.*, 2001, 73, 3193-3197.
11. D. Wood et al., *Proc, Natl, Acad, Sci. U.S.A.*, 2.010, 107 10008-10013.
12. Y. Wang et al., *Lab Chip*, 2010, 10, 2917-2924.
13. P. Gach et al., *Biomicrofluidics*, 2011, 5.
14. J. Fritz and M. Owen, *J. Adhes.*, 1995, 54, 33-45.
15. V. Jokinen et al., *Biomicrofluidics*, 2012, 6, 016501.
16. J. Kang et al., *Lab Chip*, 2008, 8, 176-178.
17. E. Bormashenko et al., *App., Phys. Let.* 2007, 90.
18. R. Moerman and G. W. K. van Dedem, *Anal. Chem.*, 2003, 75, 4132-4138.
19. H. Moeller et al., *Biomaterials*, 2008, 29, 752-763.
20. C. Hsieh et al.,*Biomed; Microdevices*, 2010, 12, 897-905.
21. D. Qin et al., at. *Nat. Protoc.*, 2010, 5, 491-502,
22. T. Datasheet, SU-8 Photoresist Formulations, http://www.microchem.com/pdf/SU8_50-100.pdf.
23. R. Horvath et al., *J. Micromech. Microeng.*, 2003, 13, 419-424.
24. A. Waltermoa et al., *Journal of Dispersion Science and Technology*, 1994, 15, 273296.
25. D. Bodas and C. Khan-Malek, *Sens, Actuator B-Chem.*, 2007, 123, 368-373.
26. S. Hu et al., *Analytical Chemistry*, 2002, 74, 4117-4123.
27. C. Ishino et al., *Europhys. Let.t*, 2004, 68, 419-425.
28. M. Abdelsalam et al, *Langmuir*, 2005, 21, 1753-1757.
29. D. Quere, in *Annual Review of Materials Research*, Annual Reviews, Palo Alto, 2008, vol. 38. pp. 71-99.
30. N. A. Patankar J. *Adhes. Sci. Technol.*, 2009, 23, 413-433.
31, E. Bormashenko, *Philos, Trans. R. Soc. A-Math, Phys. Eng. Sci.*, 2010, 368, 46954711.
32. Y. Wang et al., *Anal. Chem.*, 2007, 79, 7104-7109.
33. K. Isolupa et al., *Am. J Orthod. Dentofac, Orthop.*, 1995, 107, 497-504.

The foregoing: is illustrative of the present invention, and is not to be construed as limiting thereof. The invention is defined by the following claims, with equivalents of the claims to be included therein.

That which is claimed is:

1. A microfabricated device comprising:
   a substrate material fabricated to comprise a structured surface formed therein, at least one gas-entrapping feature on the structured surface that entraps gas bubbles upon wetting said structured surface with an aqueous or non-aqueous solvent or solution, wherein the substrate material comprises an array of microwells formed therein; and
   a sacrificial residue in contact with the at least one gas-entrapping feature, wherein the sacrificial residue is soluble in an aqueous or non-aqueous solvent or solution,
   wherein the sacrificial residue is configured to cause dissolution guided wetting upon contact with the aqueous or non-aqueous solvent or solution to thereby fill the at least one gas-entrapping feature without entrapping gas bubbles.

2. The device of claim 1, wherein said gas-entrapping feature comprises a well, corner, microcavity, dead end, post, trap, hole, passage, channel, or combination thereof.

3. The device of claim 1, wherein said device is comprised of an organic polymer.

4. The device of claim 1, wherein said substrate is comprised of a polymer selected from the group consisting of as polymethylmethacrylate (PMMA), polycarbonate, polytetrafluoroethylene (PTFE), polyvinylchloride (PVC), polydimethylsiloxane (PDMS), polysulfone, polystyrene, polymethylpentene, polypropylene, polyethylene, polyvinylidine fluoride, acrylonitrile-butadiene-styrene copolymer (ABS), polymerized photoresists, and combinations thereof.

5. The device of claim 1, wherein the sacrificial residue is dissolvable in the aqueous solvent or solution and is comprised of a salt, carbohydrate, hydrophilic polymer, dextran, polyethylene glycol, alginate, agarose, chitosan, glucose, sucrose, non-metabolizable carbohydrate, or sorbitol.

6. The device of claim 1, wherein the sacrificial residue is dissolvable in the non-aqueous solvent or solution and is comprised of a hydrophobic polymer, low molecular weight organic solid, non-volatile liquid, polyethylene, polypropylene, polyvinyl chloride, polystyrene, nylon, polyester, acrylic, polyurethane, polycarbonate, polylactic acid, poly (lactic-co-glycolic acid), poly(methyl methacrylate), paraffin wax, naphthalene, anthracene, aspirin (acetylsalicylic acid), 2-naphthol, fat, synthetic oil, mineral oil, vegetable oil, olive oil, lipid, silicone oil, or liquid epoxy resin.

7. A method of priming a microfabricated device for dissolution guided wetting of gas-entrapping features, comprising:
   (a) providing a microfabricated device comprising a substrate material fabricated to comprise a structured surface formed therein, at least one gas-entrapping feature on the structured surface that entraps gas bubbles upon wetting the structured surface with an aqueous or non-aqueous solvent or solution, wherein the substrate material comprises an array of microwells formed therein;
   (b) applying a sacrificial residue to the at least one gas-entrapping feature on the structured surface, wherein the sacrificial residue is soluble in an aqueous or non-aqueous solvent or solution, wherein the sacrificial residue becomes dissolved in the aqueous or non-aqueous solvent or solution upon wetting the structured surface thereby inhibiting the entrapment of gas bubbles therein through dissolution guided wetting.

8. The method of claim 7, wherein the sacrificial residue comprises a solute dissolved or dispersed in a second solvent or solution and the applying comprises contacting the solute dissolved or dispersed in the second solvent or solution with the at least one gas-entrapping feature, and allowing the second solvent or solution to dry thereon thereby depositing the solute in contact with the gas-entrapping feature.

9. The method of claim 7, wherein the sacrificial residue is applied to the at least one gas-entrapping feature as a fine particulate dust.

10. The method of claim 7, wherein the device is comprised of an organic polymer.

11. The method of claim 7, wherein the substrate is comprised of a polymer selected from the group consisting of as polymethylmethacrylate (PMMA), polycarbonate, polytetrafluoroethylene (PTFE), polyvinylchloride (PVC), polydimethylsiloxane (PDMS), polysulfone, polystyrene, polymethylpentene, polypropylene, polyethylene, polyvinylidine fluoride, acrylonitrile-butadiene-styrene copolymer (ABS), polymerized photoresists, and combinations thereof.

12. The method of claim 7, wherein the sacrificial residue is dissolvable in the aqueous solvent or solution and is comprised of dextran, polyethylene glycol, alginate, agarose, chitosan, glucose, sucrose, non-metabolizable carbohydrate, or sorbitol.

13. The method of claim 7, further comprising treating the microfabricated device with plasma oxidation prior to applying the sacrificial residue to the at least one gas-entrapping feature on the structured surface.

14. The method of claim 7, wherein the sacrificial residue is dissolvable in the non-aqueous solvent or solution and is comprised of a hydrophobic polymer, low molecular weight organic solid, non-volatile liquid, polyethylene, polypropylene, polyvinyl chloride, polystyrene, nylon, polyester, acrylic, polyurethane, polycarbonate, polylactic acid, poly (lactic-co-glycolic acid), poly(methyl methacrylate), paraffin wax, naphthalene, anthracene, aspirin (acetylsalicylic acid), 2-naphthol, fat, synthetic oil, mineral oil, vegetable oil, olive oil, lipid, silicone oil, or liquid epoxy resin.

15. The method of claim 7, wherein the microwells further comprise a releasable element positioned at the bottom of each of the microwells.

16. A method of wetting a microfabricated device while inhibiting the entrapment of gas bubbles therein, comprising:
   (a) providing a microfabricated device comprising a substrate material fabricated to comprise a structured surface formed therein, wherein the substrate material comprises an array of microwells formed therein, at least one gas-entrapping feature on the structured surface that entraps gas bubbles upon wetting the structured surface with an aqueous or non-aqueous solvent or solution, and a sacrificial residue in contact with the at least one gas-entrapping feature, wherein the sacrificial residue is soluble in an aqueous or non-aqueous solvent or solution; and
   (b) treating the microfabricated device with the aqueous or non-aqueous solvent or solution sufficient to dissolve and remove the sacrificial residue from the at least one gas-entrapping feature while concurrently wetting the at least one gas-entrapping feature with the solvent or solution thereby inhibiting the entrapment of gas bubbles therein through dissolution guided wetting.

17. The method of claim 16, wherein the aqueous solvent or solution comprises a growth media, an assay or reagent media, or a reaction media.

18. The method of claim 16, wherein the gas-entrapping feature comprises a well, corner, microcavity, dead end, post, trap, hole, passage, channel, or combination thereof.

19. The method of claim 16, wherein the microwells further comprise a releasable element positioned at the bottom of each of the microwells.

20. The method of claim 16, wherein the device is comprised of an organic polymer.

21. The method of claim 16, wherein the substrate is comprised of a polymer selected from the group consisting of as polymethylmethacrylate (PMMA), polycarbonate, polytetrafluoroethylene (PTFE), polyvinylchloride (PVC), polydimethylsiloxane (PDMS), polysulfone, polystyrene, polymethylpentene, polypropylene, polyethylene, polyvinylidine fluoride, acrylonitrile-butadiene-styrene copolymer (ABS), polymerized photoresists, and combinations thereof.

22. The method of claim 16, wherein the sacrificial residue is dissolvable in the aqueous solvent or solution and is comprised of a salt, carbohydrate, hydrophilic polymer, dextran, polyethylene glycol, alginate, agarose, chitosan, glucose, sucrose, non-metabolizable carbohydrate, or sorbitol.

23. The method of claim 16, wherein the sacrificial residue is dissolvable in the non-aqueous solvent or solution and is comprised of a hydrophobic polymer, low molecular weight organic solid, non-volatile liquid, polyethylene, polypropylene, polyvinyl chloride, polystyrene, nylon, polyester, acrylic, polyurethane, polycarbonate, polylactic acid, poly(lactic-co-glycolic acid), poly(methyl methacrylate), paraffin wax, naphthalene, anthracene, aspirin (acetylsalicylic acid), 2-naphthol, fat, synthetic oil, mineral oil, vegetable oil, olive oil, lipid, silicone oil, or liquid epoxy resin.

* * * * *